(12) United States Patent
Yang et al.

(10) Patent No.: US 10,758,733 B2
(45) Date of Patent: Sep. 1, 2020

(54) IMPLANTABLE MEDICAL DEVICE WITH RETRACTABLE FIXATION SHEATH

(71) Applicant: Medtronic, Inc., Minneapolis, MN (US)

(72) Inventors: Zhongping Yang, Woodbury, MN (US); Thomas A. Anderson, New Hope, MN (US); Yong K. Cho, Excelsior, MN (US); Becky L. Dolan, Chisago, MN (US); Rick D. Mcvenes, Isanti, MN (US)

(73) Assignee: Medtronic, Inc., Minneapolis, MN (US)

( * ) Notice: Subject to any disclaimer, the term of this patent is extended or adjusted under 35 U.S.C. 154(b) by 280 days.

(21) Appl. No.: 15/705,690

(22) Filed: Sep. 15, 2017

(65) Prior Publication Data

US 2019/0083801 A1    Mar. 21, 2019

(51) Int. Cl.
| | | |
|---|---|---|
| *A61N 1/37* | (2006.01) | |
| *A61N 1/375* | (2006.01) | |
| *A61N 1/05* | (2006.01) | |
| *A61N 1/362* | (2006.01) | |

(52) U.S. Cl.
CPC ....... *A61N 1/37518* (2017.08); *A61N 1/0573* (2013.01); *A61N 1/362* (2013.01); *A61N 1/3756* (2013.01); *A61N 1/37512* (2017.08)

(58) Field of Classification Search
CPC .................................................. A61N 1/37518
USPC .................................................. 606/126–128
See application file for complete search history.

(56) References Cited

U.S. PATENT DOCUMENTS

| | | |
|---|---|---|
| 5,575,814 A | 11/1996 | Giele et al. |
| 6,687,550 B1 | 2/2004 | Doan |
| 7,027,876 B2 | 4/2006 | Casavant et al. |
| 7,532,933 B2 | 5/2009 | Hastings et al. |
| 7,840,283 B1 * | 11/2010 | Bush .................... A61N 1/0573 607/127 |
| 7,860,581 B2 | 12/2010 | Eckerdal et al. |
| 7,991,484 B1 | 8/2011 | Sengupta et al. |
| 8,332,036 B2 | 12/2012 | Hastings et al. |
| 8,352,028 B2 | 1/2013 | Wenger |
| 8,478,408 B2 | 7/2013 | Hastings et al. |
| 8,620,458 B1 | 12/2013 | Sengupta et al. |

(Continued)

OTHER PUBLICATIONS (PCT/US2018/051180) PCT Notification of Transmittal of the International Search Report and the Written Opinion of the International Searching Authority, dated Nov. 15, 2018, 10 page.

(Continued)

*Primary Examiner* — Lynsey C Eiseman

(57) ABSTRACT

An implantable medical device has a housing having a proximal end, a distal end and an outer sidewall extending from the proximal end to the distal end. A fixation sheath includes a housing sheath portion extending along the outer sidewall of the housing, and a fixation member portion extending from the housing sheath portion. The housing sheath portion is advanceable from a first position along the outer sidewall of the housing in which the fixation member portion is retracted toward the proximal end of the housing to a second position along the outer sidewall of the housing in which the fixation member portion is deployed to extend away from the housing distal end for anchoring the implantable medical device at an implant site.

30 Claims, 11 Drawing Sheets

(56) References Cited

U.S. PATENT DOCUMENTS

| | | | |
|---|---|---|---|
| 8,781,605 B2 | 7/2014 | Bomzin et al. | |
| 8,948,883 B2 | 2/2015 | Eggen et al. | |
| 9,072,911 B2 | 7/2015 | Hastings et al. | |
| 9,119,959 B2 | 9/2015 | Rys et al. | |
| 9,155,882 B2 | 10/2015 | Grubac et al. | |
| 9,283,381 B2 | 3/2016 | Grubac et al. | |
| 9,393,424 B2 | 7/2016 | Demmer et al. | |
| 9,399,139 B2 | 7/2016 | Demmer et al. | |
| 9,492,668 B2 | 11/2016 | Sheldon et al. | |
| 9,492,669 B2 | 11/2016 | Demmer et al. | |
| 9,504,829 B2 | 11/2016 | Spinelli et al. | |
| 9,517,336 B2 | 12/2016 | Eggen et al. | |
| 9,526,891 B2 | 12/2016 | Eggen et al. | |
| 9,579,500 B2 | 2/2017 | Rys et al. | |
| 2011/0251662 A1* | 10/2011 | Griswold | A61N 1/37205 607/128 |
| 2011/0270339 A1 | 11/2011 | Murray, III et al. | |
| 2011/0270340 A1 | 11/2011 | Pellegrini et al. | |
| 2012/0172690 A1 | 7/2012 | Anderson et al. | |
| 2012/0172892 A1* | 7/2012 | Grubac | A61N 1/3756 606/129 |
| 2012/0191169 A1 | 7/2012 | Rothstein et al. | |
| 2014/0180306 A1 | 6/2014 | Grubac et al. | |
| 2016/0001068 A1 | 1/2016 | Grubac et al. | |
| 2016/0015287 A1 | 1/2016 | Anderson et al. | |
| 2016/0015322 A1 | 1/2016 | Anderson et al. | |
| 2016/0059002 A1 | 3/2016 | Grubac et al. | |
| 2016/0243350 A9 | 8/2016 | Grubac et al. | |
| 2017/0056670 A1 | 3/2017 | Sheldon et al. | |

OTHER PUBLICATIONS

Chen et al., "Interventional Medical Devices, Device Systems, and Fixation Components Thereof", U.S. Appl. No. 15/410,161, filed Jan. 19, 2017, 39 pages.

* cited by examiner

IMPLANTABLE MEDICAL DEVICE WITH RETRACTABLE FIXATION SHEATH

TECHNICAL FIELD

This disclosure relates generally to implantable medical devices and in particular to an implantable medical device having a housing and a fixation sheath that is retractable and advanceable over the housing.

BACKGROUND

Implantable medical devices (IMDs) may be provided for monitoring a physiological condition or signal and/or delivering a therapy to a patient. Examples of IMDs include pacemakers, cardioverter defibrillators, cardiac monitors which may monitor hemodynamic function and/or cardiac electrical signals, neurological stimulators, insulin monitors, oxygen monitors, pressure monitors, drug delivery pumps and more. Generally, IMDs may be equipped with a fixation device or mechanism that anchors the IMD at a desired implant site. The fixation device or mechanism may provide passive fixation that stabilizes the IMD position by passively pressing against or interacting with the body tissue or anatomical structures at the implant site without piercing the patient's tissue. In other examples, the fixation device or mechanism may provide active fixation that anchors the IMD in position by piercing or penetrating the patient's body tissue at the implant site. Stable positioning of the IMD at a desired implant site is generally important in ensuring beneficial and reliable function of the IMD.

In some clinical applications, an IMD may be tested or physiological signals may be acquired at multiple anatomical sites before an optimal implant site for the IMD is selected, based on the testing or acquired physiological signals. The fixation device may make repositioning of the IMD from one test site to another test site difficult or challenging. At least in the case of active fixation devices, moving an IMD between multiple sites for testing may cause undesired tissue injury at the multiple sites.

SUMMARY

In general, this disclosure is directed to an IMD having a fixation sheath that is advanceable and retractable along a housing of the IMD. The fixation sheath has a fixation member portion that may be maintained in a retracted position to avoid or minimize contact with patient body tissue during implant and testing procedures. The retracted position of the fixation sheath allows the IMD to be moved to multiple testing sites within a patient without fixation of the IMD or any associated tissue injury. After selecting a desired implant site, the fixation sheath may be advanced from the retracted position to an advanced position to deploy the fixation member portion and thereby anchor the IMD at the selected implant site.

In one example, the disclosure provides an implantable medical device having a housing for enclosing electronic circuitry of the implantable medical device. The housing has a proximal end, a distal end and an outer sidewall extending from the proximal end to the distal end. A fixation sheath includes a housing sheath portion extending along the housing outer sidewall and a fixation member portion extending from the housing sheath portion. The housing sheath portion is advanceable from a first position along the housing outer sidewall in which the fixation member portion is retracted toward the proximal end of the housing to a second position along the housing outer sidewall in which the fixation member portion is deployed to extend away from the housing distal end for anchoring the implantable medical device at an implant site.

In another example, the disclosure provides a fixation sheath for an implantable medical device including a housing sheath portion configured to extend along an outer sidewall of a housing of the implantable medical device that encloses electronic circuitry of the implantable medical device. The fixation sheath includes a fixation member portion extending from the housing sheath portion. The housing sheath portion is advanceable from a first position along the housing outer sidewall in which the fixation member portion is retracted toward a proximal end of the housing to a second position along the housing outer sidewall in which the fixation member portion is deployed to extend away from a distal end of the housing for anchoring the implantable medical device at an implant site.

In yet another example, the disclosure provides an implantable medical device system including an implantable medical device and a delivery tool. The implantable medical device includes a housing having a proximal end, a distal end and an outer sidewall extending from the proximal end to the distal end and a fixation sheath. The fixation sheath includes a housing sheath portion extending along the housing outer sidewall, a fixation member portion extending from the housing sheath portion, and a delivery tool interface member coupled to the housing sheath portion. The housing sheath portion is advanceable from a first position along the housing outer sidewall in which the fixation member portion is retracted toward the proximal end of the housing to a second position along the housing outer sidewall in which the fixation member portion is deployed to extend away from the housing distal end for anchoring the implantable medical device at an implant site. The delivery tool includes a receptacle for retaining the housing with the fixation sheath in the first position and an advancement tool configured to engage the delivery tool interface member and advance the sheath from the first position to the second position to deploy the fixation member portion to anchor the implantable medical device at an implant site.

This summary is intended to provide an overview of the subject matter described in this disclosure. It is not intended to provide an exclusive or exhaustive explanation of the apparatus and methods described in detail within the accompanying drawings and description below. Further details of illustrative examples are set forth in the accompanying drawings and the description below.

DETAILED DESCRIPTION

An IMD having a fixation sheath is disclosed herein. The fixation sheath may circumscribe the IMD housing and may be advanceable from a first position in which a fixation member portion of the fixation sheath is retracted, e.g., alongside the housing, to a second position in which the fixation member is deployed to extend away from the IMD housing and anchor the IMD at an implant site by engaging with tissue at the implant site. In some clinical applications, it is desirable to obtain physiological signals or test therapy efficacy at one or more sites within a patient's body in order to select an optimal site for patient monitoring and/or therapy delivery. The advanceable and retractable fixation sheath disclosed herein allows an IMD to be delivered to a test site for acquiring a physiological signal and/or test a response to a delivered therapy or stimulus, e.g., one or more electrical stimulation pulses or a pharmaceutical agent, without deployment of the fixation member. Upon selecting an implant site, the fixation sheath is advanced from a retracted position along the IMD housing to deploy the fixation member portion and anchor the IMD at the implant site.

In the illustrative examples presented herein, the IMD is described as being a pacemaker having at least two electrodes for delivering cardiac pacing pulses and/or sensing cardiac electrical signals. The pacemaker is a leadless pacemaker in the examples provided herein, e.g., an intracardiac leadless pacemaker. It is recognized however, that aspects of a fixation sheath and corresponding aspects of the IMD housing and/or a delivery tool used to advance and retract the fixation sheath and deliver the IMD to a test or implant site may be implemented in conjunction with a variety of IMDs, including but not limited to implantable cardioverter defibrillators, cardiac monitors, blood chemistry monitors, pressure monitors, oxygen monitors, drug pumps, neurological stimulators used to deliver stimulation to the central or peripheral nervous system, and smooth or skeletal muscle stimulators.

Figure 1A:
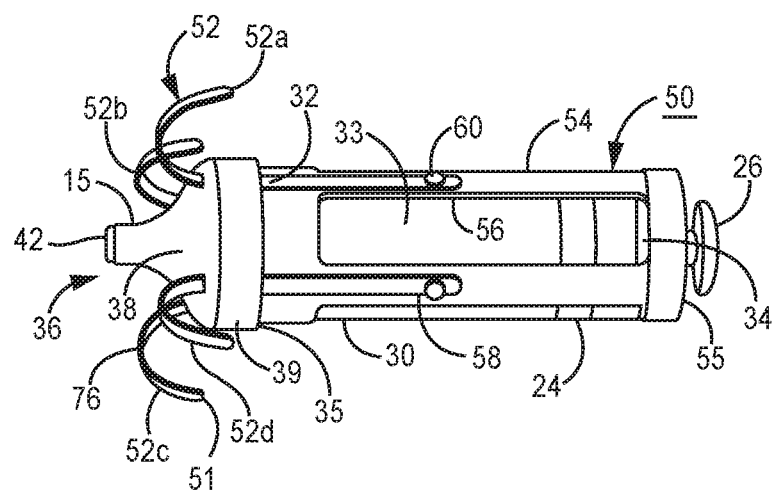
FIG. 1A is a perspective view of an IMD having a retractable fixation sheath according to one example.

FIG. 1A is a perspective view of an IMD having a fixation sheath according to one example. The IMD shown in FIG. 1A is a leadless, intracardiac pacemaker 10. Pacemaker 10 includes a housing 30, a fixation sheath 50 and a distal assembly 36 coupled to the distal end 32 of housing 30. Housing 30 includes an outer sidewall 33 extending from a housing distal end 32 to a housing proximal end 34. Housing 30 is generally cylindrical in the examples presented herein but may be prismatic in other examples, e.g., having parallel distal and proximal ends 32 and 34 separated by three or more longitudinal outer sidewalls instead of the cylindrical outer sidewall shown in FIG. 1A.

Housing 30 defines a hermetically sealed internal cavity in which internal components of pacemaker 10 reside, such as a sensing circuit, therapy delivery circuit, control circuit, memory, telemetry circuit, other optional sensors, and a power source. In other examples, the housing of an IMD having a retractable and advanceable fixation sheath may enclose electronic circuitry configured to perform the monitoring and/or therapy delivery function(s) according to the particular type of IMD and clinical condition being monitored or treated.

The housing 30 may be formed from an electrically conductive material including titanium or titanium alloy, stainless steel, MP35N (a non-magnetic nickel-cobalt-chromium-molybdenum alloy), or other bio-compatible metal or metal alloy. In other examples, housing 30 is formed from a non-conductive material including ceramic, glass, sapphire, silicone, polyurethane, epoxy, acetyl co-polymer plastics, polyether ether ketone (PEEK), a liquid crystal polymer, or other biocompatible polymer or any combination of one or more electrically non-conductive and/or one or more electrically conductive materials.

Figure 1B:
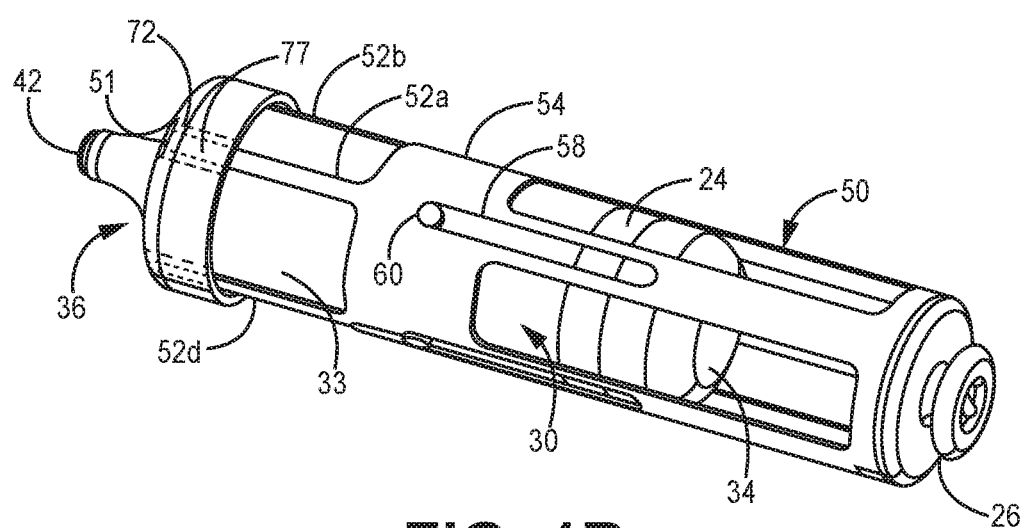
FIG. 1B is a perspective view of the IMD of FIG. 1 with the fixation sheath in a fully retracted position.

Fixation sheath 50 includes a fixation member portion 52 and a housing sheath portion 54. In some examples, fixation sheath 50 may include a delivery tool interface member 26, e.g., defining a proximal end 55 of fixation sheath 50. The delivery tool interface member 26 may be provided for engaging with a delivery tool during implantation of pacemaker 10 as described below in conjunction with FIGS. 5A-7. Housing sheath portion 54 extends from the sheath proximal end 55 to fixation member portion 52 and forms a slidable fit with housing outer sidewall 33 such that fixation sheath 50 is smoothly advanceable and retractable in distal and proximal directions relative to housing 30. In the view of FIG. 1A, fixation sheath 50 is fully advanced in the distal direction relative to housing 30 and is retractable from the fully-advanced position shown in FIG. 1A toward the housing proximal end 34 to a fully-retracted position as shown in FIG. 1B.

Housing 30 may include one or more guide members, shown as guide posts 60, along the exterior, longitudinal outer sidewall 33 of housing 30. Housing sheath portion 54 may define one or more guide channels 58 that slide or glide along guide posts 60 as fixation sheath 50 is longitudinally advanced or retracted along housing 30. Posts 60 and guide channels 58 interact to prevent twisting or rotation of housing sheath portion 54 relative to housing 30 in the example shown and may prevent over-advancement and/or over-retraction of fixation sheath 50. In other examples, a longitudinal groove or channel may be formed along the longitudinal outer sidewall 33 of housing 30, and housing sheath portion 54 may include an inwardly protruding post, ridge or other protruding guide member that glides within the groove or channel of the housing longitudinal outer sidewall 33.

Fixation member portion 52 extends from housing sheath portion 54. Fixation member portion 52 may include one or more fixation tines 52a-d. Each fixation tine 52a-d may possess a curved portion 76 when in a normally curved tine position as shown in FIG. 1A. Fixation sheath 50 may be formed from a shape memory material, e.g., Nitinol, such that fixation member tines 52a-d may be heat set to retain the normally curved position shown when not subjected to external forces. Each fixation tine 52a-d may be elastically deformable from the normally curved position, corresponding to an advanced position of fixation sheath 50 shown in FIG. 1A, to an extended position, corresponding to the retracted position of the fixation sheath 50 as shown in FIG. 1B. During deployment of the fixation member portion 52, the distal tips 51 of the tines 52a-d penetrate the heart tissue to a limited depth before elastically curving back proximally into the normally curved position as shown in FIG. 1A, upon being advanced from a retracted position and being released from the confines of a delivery tool. Aspects of fixation member tines 52a-d may generally correspond to the fixation member disclosed in U.S. 2016/0059002 A1 (Grubac, et al.) or in U.S. Pat. No. 9,119,959 (Rys et al.), both of which are incorporated herein by reference in their entirety.

Pacemaker 10 includes a distal assembly 36 coupled to housing distal end 32. Distal assembly 36 may include one or more electrodes, e.g., a tip electrode 42 which may be mounted on a distal extension 15 of assembly 36. Tip electrode 42 may be a hemispherical, flat, ring, helical, conical or other electrode type that is held in intimate contact, against or in close proximity to, a pacing or sensing site when fixation member portion 52 is deployed to anchor pacemaker 10 at the pacing or sensing site. Distal assembly 36 carrying a tip electrode 42 may include a tip electrode as generally disclosed in U.S. patent application Ser. No. 15/410,161 (Chen, et al.), incorporated herein by reference in its entirety. In other examples, distal assembly 36 may include a tissue-piercing electrode that is configured to pierce and penetrate cardiac tissue for advancement to a pacing site at a desired depth within the cardiac chamber wall, e.g., within the ventricular septum, a ventricular free wall, an atrial free wall, the atrial septum or cardiac anatomical structure. For instance, distal assembly 36 may include a dart electrode having a shaft and tip electrode 42 that penetrates into cardiac tissue as generally disclosed in U.S. patent application Ser. No. 16/130,272, incorporated herein by reference in its entirety.

In some cases distal tip electrode 42 may be implemented as an active fixation electrode such as a helical, barbed, or hooked electrode for both penetrating cardiac tissue and providing active fixation of tip electrode 42 within the cardiac tissue at a pacing and sensing site. In other cases, tip electrode 42 does not include a fixation feature but is capable of piercing cardiac tissue, e.g., by having a narrow diameter or relatively pointed tip. In still other examples, tip electrode 42 has a smooth, rounded, and/or relatively larger diameter tip configured to be held against endocardial tissue at a pacing and/or site by fixation member tines 52a-d, without penetration of tip electrode 42 into the cardiac tissue.

In some examples, distal tip electrode 42 may function as a cathode electrode for pacing and sensing at a pacing site. All or a portion of housing 30 may function as a return anode electrode 24 during pacing and/or sensing. Housing sheath portion 54 may define one or more windows 56 for exposing all or at least a portion of proximal housing-based electrode 24 to the surrounding environment for effective pacing and sensing.

Housing 30 may include one or more housing-based electrodes. In the example shown, a housing-based electrode 24 is shown to circumscribe a proximal portion of housing outer sidewall 33. When housing 30 is formed from an electrically conductive material, such as a titanium alloy or other examples listed above, portions of housing 30 may be electrically insulated by a non-conductive material, such as a coating of parylene, polyurethane, silicone, epoxy or other biocompatible polymer, leaving one or more discrete areas of conductive material exposed to define proximal housing-based electrode 24. When housing 30 is formed from a non-conductive material, such as a ceramic, glass or polymer material, an electrically-conductive coating or layer, such as a titanium, platinum, stainless steel, or alloys thereof, may be applied to one or more discrete areas of housing 30 to form a housing-based electrode 24. In other examples, housing-based electrode 24 may be a component, such as a ring electrode, that is mounted or assembled onto housing 30. Housing-based electrode 24 may be electrically coupled to internal circuitry of pacemaker 10 via electrically-conductive housing 30 or an electrical conductor when housing 30 is a non-conductive material. In the example shown, housing-based electrode 24 is located nearer to housing proximal end 34 than housing distal end 32 and is therefore referred to as a "proximal housing-based electrode" 24. In other examples, however, a housing-based electrode 24 may be located at other positions along housing 30, e.g., more distally than the position shown.

Housing 30 may include one or more housing-based electrodes extending along housing 30, which may be electrically tied together or electrically isolated from one another. For instance, when housing 30 is formed of an electrically conductive material, portions of housing 30 may be covered by an electrically insulating material, such as parylene, leaving two or more areas of housing 30 exposed as electrically conductive surfaces of the housing-based electrode. In other instances, housing 30 may be formed from a non-conductive material with two or more electrically isolated electrodes carried by the housing.

In other examples, distal assembly 36 may include a distal housing-based electrode (not shown in the example of FIG. 1A). For example, a ring electrode may extend along the distal surface 38 of distal assembly 36 or circumscribe the outer surface 39 of distal assembly 36. A distal housing-based electrode may serve as a return anode electrode paired with tip electrode 42 for sensing cardiac electrical signals, such as P-waves attendant to atrial depolarizations or R-waves attendant to ventricular depolarizations, depending on the implant site of pacemaker 10 and tip electrode 42, and/or for delivering pacing pulses. In other examples, a distal housing-based electrode carried by assembly 36 may be a cathode electrode for sensing cardiac electrical signals and delivering pacing pulses at an endocardial pacing site, particularly when tip electrode 42 is a tissue penetrating tip electrode that is advanced to a pacing site spaced apart from the endocardial site adjacent to assembly distal surface 38. When the housing-based distal electrode serves as a cathode electrode, the proximal housing-based electrode 24 may serve as the return anode paired with tip electrode 42 for pacing and/or sensing at one pacing/sensing site and as the return anode paired with distal housing-based electrode carried by distal assembly 36 for pacing and/or sensing at a second pacing/sensing site, as generally disclosed in the above-incorporated U.S. patent application Ser. No. 16/130, 272.

In other examples, distal assembly 36 may include one or more other sensors, in addition to or instead of electrode 42.

Other sensors may include, with no limitation intended, an oxygen sensor, pressure sensor, accelerometer, pH sensor, temperature sensor, glucose sensor, acoustical sensor, or optical sensor.

FIG. 1B is a perspective view of pacemaker 10 with fixation sheath 50 in a fully retracted position. Distal assembly 36 includes one or more open slots 72 corresponding to the number of fixation tines 52a-d of fixation member portion 52. Each slot 72 is aligned with and sized to receive a respective one of fixation tines 52a-d. In the fully retracted position, at least a portion 77 of each fixation tine 52a-d is confined within a respective slot 72 of distal assembly 36. The portion 77 confined within each slot 72 is distal to and/or includes all or a portion of the normally curved portion 76 (FIG. 1A). In some examples, the portion 77 of each tine 52a-d held within a respective slot 72 in the fully retracted position includes the distal tine tip 51 as shown in FIG. 1B. In other examples, the distal tine tips 51 of fixation member portion 52 may protrude from slots 72 but are retracted relative to tip electrode 42 to avoid contact with body tissue at a test or candidate implant site while in the retracted position.

In this fully retracted position, the tines 52a-d may be held substantially flat against the longitudinal outer sidewall 33 of housing 30 due to the confinement of at least a portion 77 of the tines 52a-d, distal to and/or including the curved portion 76 of the tines 52a-d, within a respective slot 72. Guide posts 60 protruding from longitudinal outer sidewall 33, riding within guide channels 58 of housing sheath portion 54, prevent rotation and over-retraction of fixation sheath 50 during retraction from the fully advanced position of FIG. 1A to the fully retracted position of FIG. 1B.

Figure 2A:
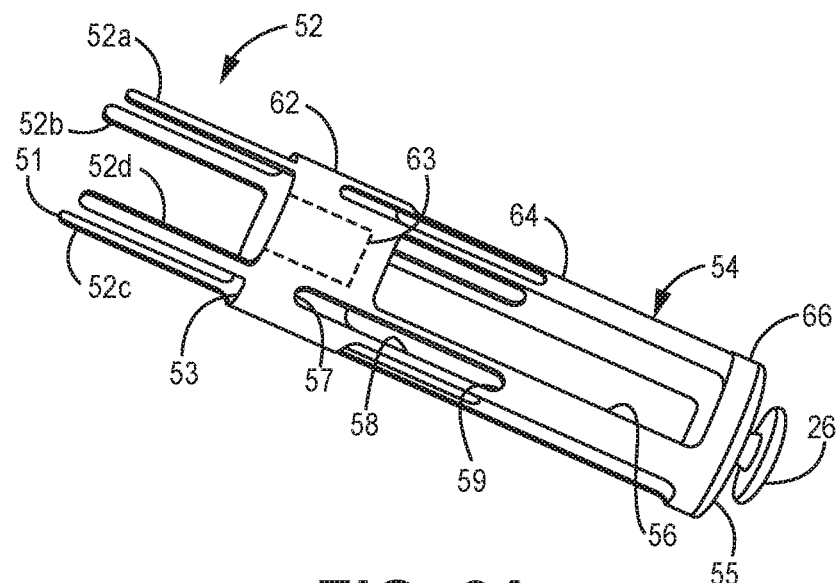
FIGS. 2A and 2B are conceptual diagrams of the fixation sheath of FIGS. 1A and 1B.
Figure 2B:
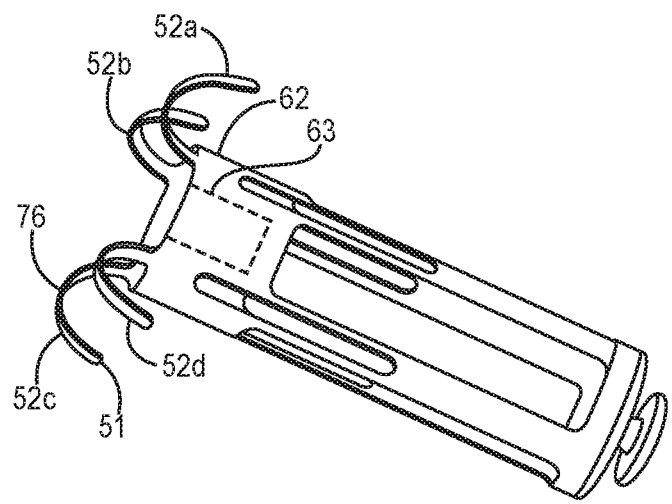

FIGS. 2A and 2B are conceptual diagrams of retractable fixation sheath 50. FIG. 2A is a perspective view of retractable fixation sheath 50 with fixation member tines 52a-d in an extended position. FIG. 2B is a perspective view of retractable fixation sheath 50 with fixation member tines 52a-d in a relaxed, normally-curved position. In some examples, fixation member portion 52 and housing sheath portion 54 may be formed as a single, unitary component. For example, fixation sheath 50 may be formed from a tubular piece of Nitinol by laser cutting to define fixation member tines 52a-d of fixation member portion 52 and various openings of housing sheath portion 54. Housing sheath portion 54 extends from a sheath portion distal end 53 to proximal end 55 and may include a distal circumferential ring 62 that circumscribes a distal portion of housing 30, a proximal circumferential ring 66 that circumscribes a proximal portion of housing 30 and a longitudinal sidewall 64 extending from distal circumferential ring 62 to proximal circumferential ring 66.

Longitudinal sidewall 64 may define various openings including one or more open guide channels 58 extending longitudinally along a portion of sidewall 64. Each guide channel 58 is provided for receiving and interacting with a respective guide post 60 protruding radially from the outer sidewall 33 of housing 30 as described above. The length of each guide channel 58 is selected to allow retraction of housing sheath in a proximal direction far enough to retract fixation tines 52a-d within the distal assembly 36 prior to deployment at an implant site. The distal end 57 of the guide channels 58 may act as a retraction stop against post 60 (FIG. 1) to prevent over-retraction of fixation sheath 50. The proximal end 59 of guide channels 58 may act as a distal stop against a guide post 60 (FIG. 1) to control the maximum distal advancement of fixation sheath 50 over housing 30 in some examples. Additionally or alternatively, the proximal end 55 of fixation sheath 50 acts as a proximal stop when it meets or butts up against the housing proximal end 34.

Guide channel 58 is shown as a linear guide channel but may be non-linear in other examples. For example, guide channel 58 may be an L-shaped guide channel having a longitudinal linear portion that enables retraction and advancement of fixation sheath 50 relative to housing 30 and an orthogonal side branch at the distal end of the longitudinal linear portion to allow the housing sheath portion 54 to be "locked" in place in the advanced position to prevent unintended retraction of the fixation sheath 50 relative to housing 30. In other examples, guide channel 58 may have a proximal, orthogonal side branch to lock the housing sheath portion 54 in the retracted position. In still other examples, guide channel 58 may have both a proximal and distal side branch to lock housing sheath portion in both the advanced and retracted positions to prevent unintended sliding of the fixation sheath 50 relative to housing 30. In still other examples, guide channel 58 may be helical, e.g., as described below in conjunction with FIG. 9, or other shapes depending at least in part on the shape and configuration of fixation member portion 52 during its deployment.

In the examples given above wherein the guide channels 58 may be non-linear, slots 72 of distal assembly 36 shown in FIG. 1B may be wider than the width of each tine 52a-d to allow tines 52a-d to move laterally within slots 72 when fixation sheath 50 is rotated relative to housing 30. Tines 52a-d may each include a horizontal or curving base portion that connects each respective tine 52a-d to the housing sheath portion 54 to enable tines 52a-d to extend straight out from the slots 72 without being twisted or deformed when fixation sheath 50 and housing 30 are rotated relative to one another as guided by non-linear guide channels.

Fixation sheath 50 may be assembled onto pacemaker housing 30 by sliding the distal fixation member portion 52 and distal circumferential ring 62 over the housing proximal end 34 with guide channels 58 aligned with guide posts 60 and tines 52a-d aligned with slots 72. Fixation sheath 50 is advanced over housing 30 until guide posts 60 are received within guide channels 58 and tines 52a-d are threaded into slots 72. In some examples, distal circumferential ring 62 may include a stress-relieving feature 63 (also referred to as an expansion relief), shown by dashed line, which may be a cut-through or cut-out region of circumferential ring 62. Stress-relieving feature 63 allows distal circumferential ring 62 to expand or flex over guide posts 60 and return to its original diameter and circumferential shape as sheath 50 is assembled onto housing 30. The stress-relieving feature 63 may include one or more cut-out slots along distal circumferential ring 62. Stress-relieving feature 63 may be narrower than the dashed area indicated in FIG. 2B and may be linear, "L" shaped or another geometry that allows housing sheath portion 54 to be elastically expanded during assembly over housing 30.

Retractable fixation sheath 50 is sized with a diameter to have clearance for advancing and retracting over housing 30 without significant friction or resistance. A parylene or other coating over housing 30 may be provided to reduce friction between the inner surface of fixation sheath 50 and outer sidewall 33 of housing 30. Longitudinal sidewall 64 is shown to circumscribe housing outer sidewall 33. In other examples, housing sheath portion 54 may extend along a portion of the circumference of housing outer sidewall 33 (or along one or more flat sidewalls in the case of a prismatic housing), without necessarily fully circumscribing the housing outer sidewall. In this case, the fixation sheath may be retained alongside the housing outer sidewall 33 by the guide posts 60, e.g., having a flared head that prevents housing sheath portion 54 from coming away from outer sidewall 33. Other retaining feature(s) may be provided along housing outer sidewall 33 for engaging with and retaining housing sheath portion alongside outer sidewall 33 while still enabling sliding of housing sheath portion 54 relative to housing 30.

Longitudinal sidewall 64 may define one or more windows 56, through which at least one housing-based electrode 24 (shown in FIGS. 1A and 1B) is exposed. In the example shown, housing sheath portion 54 includes four equally spaced guide channels 58 and four open windows 56, however fewer or more guide channels 58 and open windows 56 may be provided. Open windows 56 may extend approximately 75% of the length of housing sheath portion 54, approximately than 50% of the length of the housing sheath portion 54, or less than approximately 50% of the length of housing sheath portion 54. Open windows 56 are provided as needed for exposing a desired surface area of one or more housing-based electrodes. As such, in some examples, open windows 56 along longitudinal sidewall 64 may have a length corresponding to the length of the housing-based electrode 24 that circumscribes housing 30. Open windows 56 may be sized to expose a corresponding housing-based electrode or sensor in the advanced position of fixation sheath 50 or sized large enough to expose a housing-based electrode or sensor in both the retracted position and in the advanced position of fixation sheath 50.

In other examples, pacemaker 10 may include one or more other sensors carried by housing 30, such as a pressure sensor, oxygen sensor, acoustical sensor, temperature sensor, pH sensor, optical sensor, or any of the other examples of sensors listed herein, that require an exposed surface. In some cases, pacemaker 10 or another IMD having a retractable fixation sheath according to the present disclosure may include a therapy delivery port or outlet such as a drug delivery port that requires exposure through an open window 56 of retractable fixation sheath 50. Accordingly, housing sheath portion 54 may include one or more open windows 56, which may have varying locations along housing sheath portion 54 and varying dimensions as required to adequately expose a sensor, electrode, therapy delivery port or the like in order to enable monitoring of a physiological signal and/or delivery of a therapy as needed for a particular clinical application. The size of the open windows 56 may allow for a corresponding electrode or other sensor or therapy delivery port to be exposed in both the retracted and the advanced positions of fixation sheath 50. The maximum dimensions and locations of guide channels 58 and windows 56 are selected to preserve adequate width and length of the material of longitudinal sidewall 64 so that longitudinal sidewall 64 possesses longitudinal compressive strength and torsional strength to resist buckling and twisting when fixation member tines 52a-d are advanced into cardiac tissue.

In FIG. 2A, fixation member tines 52a-d are shown in an extended, linear position, e.g., prior to being formed into the normally-curved shape during manufacturing or when held in a stressed, extended position alongside pacemaker housing 30 when retractable fixation sheath 50 is retracted over housing 30 and fixation tines 52a-d are held within slots 72 of distal assembly 36 as shown in FIG. 1B and/or within the confines of a delivery tool. In FIG. 2B, fixation member tines 52a-d are shown in their relaxed, normally-curved position after being formed into a desired shape having curved portion 76 proximal to distal tine tip 51. As described above, retractable fixation sheath 50 may be machined from a shape memory material, such as Nitinol, such that tines 52a-d may be manipulated from an initially linear position after machining from a tubular piece of material into the desired normally-curved shape that is heat set and elastically deformable.

Figure 3:
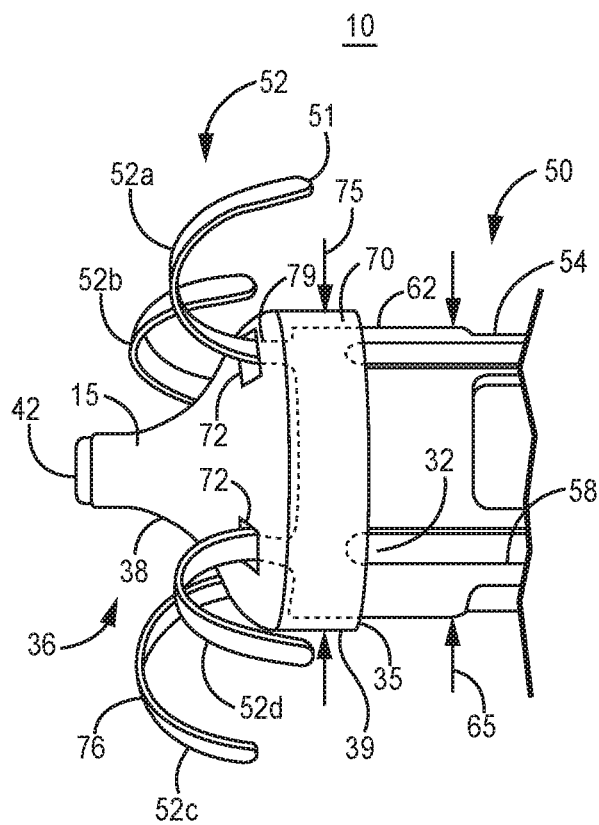
FIG. 3 is an enlarged view of a distal portion of the IMD of FIG. 1A according to one example.

FIG. 3 is an enlarged view of a distal portion of pacemaker 10 according to one example. Distal assembly 36 may include a molded or machined body 70 having distal surface 38 and circumferential surface 39. The outer diameter 75 of circumferential surface 39, or a portion thereof, may be greater than the outer diameter 65 of retractable fixation sheath 50 to define a proximal face 35 of body 70. For example, outer sidewall 33 of pacemaker housing 30 may have an outer diameter of approximately 7 mm or less, e.g. 5.7 mm to 6.7 mm. Retractable fixation sheath 50 may have an inner diameter that is 0.125 to 0.5 mm larger than the outer diameter of housing 30 to provide clearance for retraction and advancement over housing 30. Retractable fixation sheath 50 may have a wall thickness of 0.125 to 0.25 mm. The outer diameter 75 of distal assembly 36 may be approximately 0.5 to 1 mm larger than the fixation sheath outer diameter to define proximal face 35 extending radially outward from the outer diameter 65 of fixation sheath 50. It is to be understood that the illustrative examples of housing and fixation sheath dimensions provided here are not intended to be limiting and a pacemaker or other IMD having larger or smaller dimensions than the examples given here may have a retractable and advanceable fixation sheath in accordance with the present disclosure.

As described below and shown in FIGS. 5A and 5B, the proximal face 35 of distal assembly 36 is provided for mating with a distal surface of a delivery tool. Proximal face 35 is a circumferential face in FIG. 3 but may include one or more discrete surfaces, e.g., defined by one or more flanges extending radially outward. In other examples, a flange, ridge, ring or other member may protrude radially from circumferential surface 39 to define a proximal face that mates with a distal surface of the delivery tool. The proximal face 35 may act as a stop to prevent pacemaker 10 from being fully retracted within the delivery tool, thereby keeping tip electrode 42 exposed for electrophysiological testing. The proximal face 35 may also act as a surface against which force is applied by the delivery tool for advancing pacemaker 10 to a targeted test or implant site.

The distal surface 38 of assembly 36 may be molded or machined to define a distal extension 15 for supporting and extending tip electrode 42 away from distal surface 38. In other examples, distal surface 38 may be relatively flat, conical, or convex to hold tip electrode 42 at a desired height from housing distal end 32. In other examples, tip electrode 42 may be carried by a flexible extension or by a relatively stiff shaft extending from body 70, e.g., as generally disclosed in the above-incorporated U.S. patent application Ser. No. 16/130,272. Body 70 defines an open channel or slot 72 corresponding to each fixation member tine 52a-d in the example shown. The distal tip 51 of each fixation tine 52a-d is threaded into a respective slot 72 during assembly of retractable fixation sheath 50 over housing 30.

In the fully advanced position of retractable fixation sheath 50 (the position shown in FIG. 1A and FIG. 3), the fixation tines 52a-d extend through respective slots 72 and are free to regain their normally curved position. In the advanced position, only a proximal portion 79 of each tine 52a-d may be subjected to the confinement of slots 72 such that the curved portion 76 of each tine 52a-d is free to elastically regain its relaxed, normally-curved position. With retractable fixation sheath 50 in a fully retracted position, electrophysiological testing may be performed using tip electrode 42 without actively fixing pacemaker 10 at a test site. This testing without deployment of fixation tines 52a-d avoids undue tissue trauma due to fixation and removal of tines 52a-d at multiple testing or candidate implant sites. Electrophysiological mapping may be performed, e.g., to identify a desired implant site, or rule out sites that are not desired implant sites, based on intrinsic cardiac electrical signals and/or an evoked cardiac pacing response at a test site.

Figure 4:
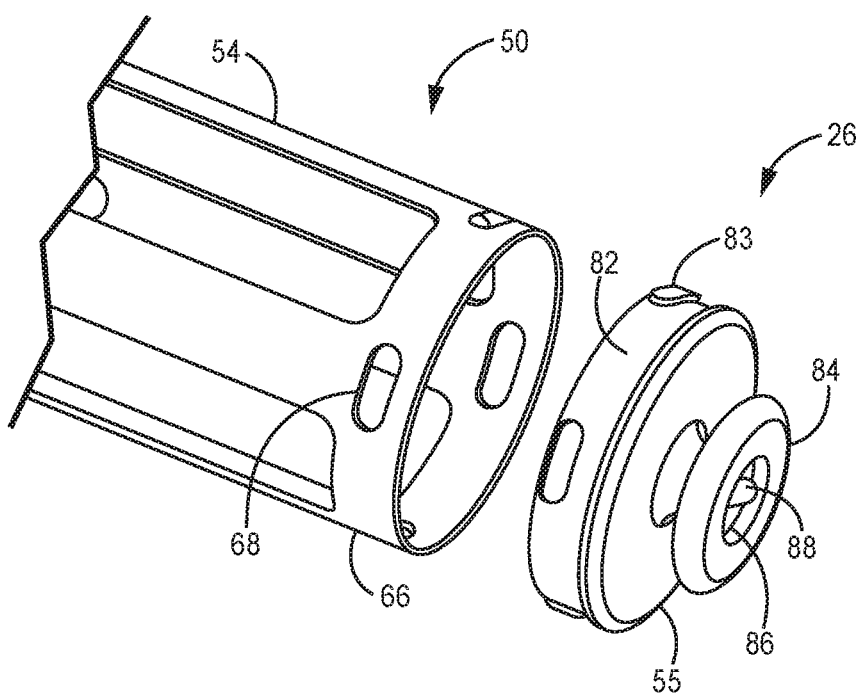
FIG. 4 is an enlarged, perspective view of a proximal portion of a fixation sheath according to one example.

FIG. 4 is an enlarged, perspective view of a proximal portion of retractable fixation sheath 50 according to one example. Fixation sheath proximal end 55 may be a closed end defined by delivery tool interface member 26. Fixation sheath proximal end 55 may serve as a stop that mates with housing proximal end 34 (shown in FIG. 1B) to prevent over-advancement of fixation sheath 50 along housing 30. In some examples, fixation sheath 50 having delivery tool interface member 26 is formed as a single, unitary body. In other examples, housing sheath portion 54 and fixation member portion 52 are machined from a tubular material as a unitary component, and delivery tool interface member 26 is provided as a separate component that is mechanically coupled, adhesively coupled, welded, or otherwise fixedly joined to the proximal circumferential ring 66 of housing sheath portion 54.

For example, delivery tool interface member 26 may be a molded component, e.g., including PEEK, silicone, polyurethane, epoxy, acetyl co-polymer plastics, a liquid crystal polymer or other plastic material. In other examples, delivery tool interface member 26 may be machined from a metal, e.g., a titanium alloy or stainless steel. Delivery tool interface member 26 may include a circumferential flange 82 and a proximal head 84. Proximal head 84 protrudes from proximal end 55 and may include a recess 86 across which a lateral beam or rod 88 extends. Proximal end 55 and/or proximal head 84 may define a proximal surface against which force is applied using a delivery tool for advancing fixation sheath 50 over housing 30. A flexible tether may be looped around lateral rod 88 for pulling back on and retracting fixation sheath 50. In other examples, a stiff tether may be configured to loop around lateral rod 88 and/or proximal head 84 for pushing (advancing) and pulling (retracting) fixation sheath 50 over housing 30 and rotating fixation sheath 50 relative to housing 50 in the case of non-linear guide channels 58.

Proximal circumferential ring 66 of housing sheath portion 54 may be sized to receive and mate with circumferential flange 82 for fixedly joining delivery tool interface member 26 to housing sheath portion 54. Circumferential flange 82 may include one or more protruding features such as nubs 83, and proximal circumferential ring 66 may include a corresponding number of apertures 68 sized to receive nubs 83 in an interlocking manner to mechanically couple delivery tool interface member 26 to housing sheath portion 54.

It is recognized that other interlocking features such as grooves, apertures, notches or other recessed, concave or open features configured to mate with corresponding ridges, bumps, knobs or other convex or protruding features may be conceived to mechanically couple delivery tool interface member 26 to housing sheath portion 54. Delivery tool interface member 26 and housing sheath portion 54 may form a snap fit that fixedly couples member 26 to housing sheath portion 54. In some examples, a medical grade adhesive such as silicone adhesive may be used to fixedly couple delivery tool interface member 26 to housing sheath portion 54. The interlocking features and/or compatible coupling methods used to fixedly attach delivery tool interface member 26 to housing sheath portion 54 will depend on the particular materials used to form member 26 and housing sheath portion 54.

Delivery tool interface member 26 may be fixedly coupled to housing sheath portion 54 so that retractable fixation sheath 50 can be advanced and retracted during a testing and implant procedure using a delivery tool engaged with interface member 26. A delivery tool may push against delivery tool interface member 26 to advance fixation sheath 50 and deploy fixation member portion 52 after identifying an implant site. In some instances, repositioning of pacemaker 10 may be required after deployment of fixation member portion 52, requiring retraction of retractable fixation sheath 50 by applying a retraction force on delivery tool interface member 26.

In other examples, delivery tool interface member 26 may be removably coupled to retractable fixation sheath 50. Delivery tool interface member 26 may be coupled to housing sheath portion 54 to provide advancement of fixation sheath 50 from the initially retracted position as shown in FIG. 1B to deploy fixation member portion 52 in the advanced position of FIG. 1A. After deployment, delivery tool interface member 26 may be withdrawn and removed from housing sheath portion 54 when the delivery tool is removed and withdrawn from pacemaker 10. In order to remove pacemaker 10 from an implanted position, the delivery tool interface member 26 may be snapped back into housing sheath portion 54 to retract fixation sheath 50, withdrawing fixation member portion 52 from cardiac tissue at the implant site.

Figure 5A:
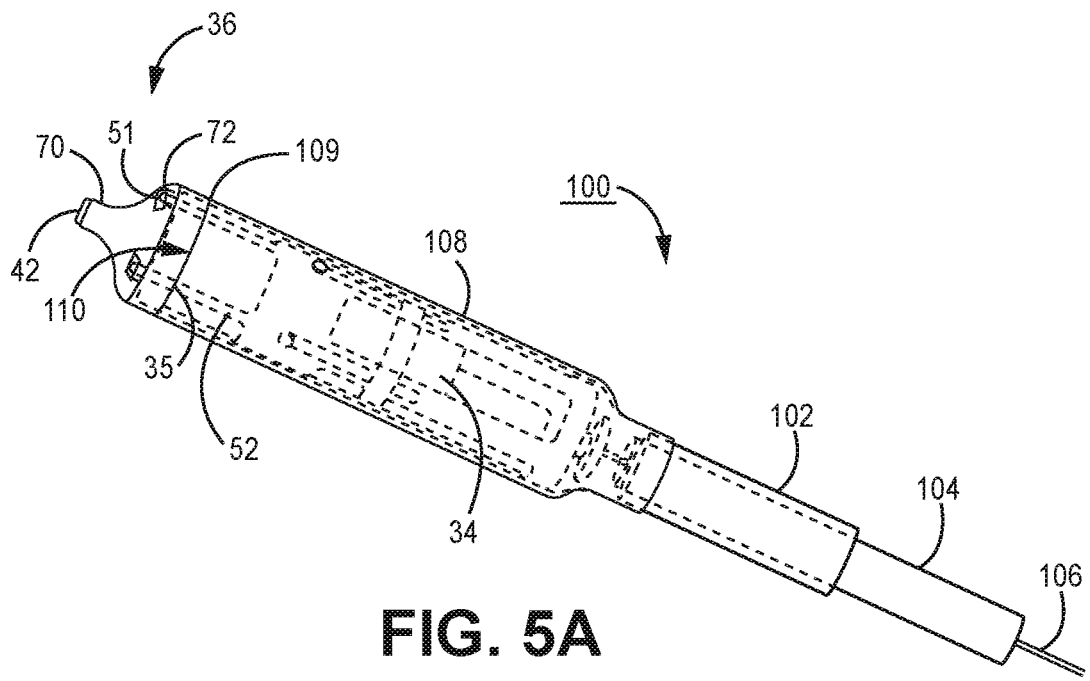
FIG. 5A is a perspective view and FIG. 5B is a sectional view of the IMD of FIG. 1A loaded within a delivery tool according to one example.
Figure 5B:
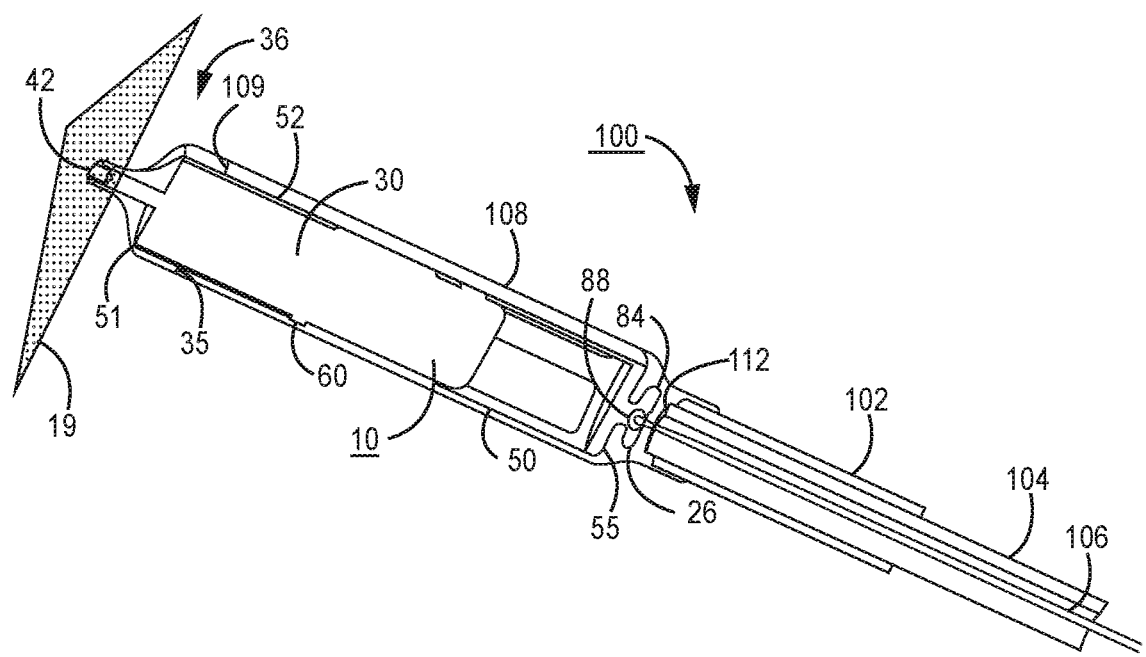

FIG. 5A is a perspective view and FIG. 5B is a sectional view of pacemaker 10 loaded within a delivery tool 100 according to one example. Delivery tool 100 includes a receptacle 108 for receiving pacemaker 10 via a distal opening 110. Pacemaker 10 is retained within receptacle 108 during advancement to a test or implant site. Receptacle 108 is coupled to the distal end of an outer catheter 102 having an open lumen through which an advancement tool 104 extends. As seen in FIG. 5B, receptacle 108 has a distal face 109, e.g., defined by the wall thickness of receptacle 108, that interfaces with proximal face 35 of distal assembly 36. Mating of the distal face 109 and proximal face 35, which are both circumferential in the examples shown, prevents pacemaker 10 from being over-retracted into receptacle 108 and may serve as a pushing interface for advancing pacemaker 10 to a candidate implant site.

Distal face 109 may push against proximal face 35 during advancement of delivery tool 100 along an implant pathway, e.g., along a transvenous or subcutaneous pathway. As described above, in other examples, distal assembly 36 may have other structures or members defining a proximal face that interfaces with a corresponding distal face of delivery tool 110. In other examples, receptacle 108 may include an outwardly extending lip, flange, ring, ridge or other member or structure that defines a distal face that mates with a correspondingly sized and shaped proximal face of pacemaker 10 for acting as a stop for preventing over-retracting of pacemaker 10 into receptacle 108 and/or as pushing interface to facilitate advancement of pacemaker 10 to an implant site.

Distal end 112 (FIG. 5B) of advancement tool 104 is sized to interface with delivery tool interface member 26 of pacemaker 10. In this example, the wall thickness of the advancement tool 104 defines the advancement tool distal end 112 that forms a circumferential pushing surface that interfaces with delivery tool interface member 26. In other examples, the distal end 112 of advancement tool 104 may include a cup, cone or other contoured or flattened pushing surface configured to mate with the corresponding geometry of delivery tool interface member 26, e.g., along the proximal end 55 and/or proximal head 84 protruding from proximal end 55.

In the fully retracted position of fixation sheath 50, tines 52a-d of fixation member portion 52 are held in a relatively flattened position alongside pacemaker housing 30, within the confines of receptacle 108. Tines of fixation member portion 52 may be pressed flush against housing 30 by the inner surface of receptacle 108. In other examples, retraction within slots 72 holds tines 52a-d in a flattened extended position alongside housing 30. The tip 51 of each respective tine 52a-d may be fully retracted within each respective slot 72 of distal assembly body 70. Tine tips 51 are shown at the distal opening of each respective slot 72 in FIG. 5A. In other examples, tine tips 51 may reside further proximally, fully within each slot 72, when fixation sheath 50 is fully retracted over housing 30 or extend slightly out of each respective slot 72.

When advancement tool 104 is advanced distally through the open lumen of outer catheter 102, its distal end 112 applies a longitudinal force against fixation sheath 50 causing fixation sheath 50 to advance longitudinally over housing 30. Advancement of fixation sheath 50 over housing 30 is guided by posts 60 protruding from housing 30 within guide channels 58 of the housing sheath portion 54 (as described above in conjunction with FIG. 1A). When fixation sheath 50 is fully advanced over housing 30, such that proximal end 55 of fixation sheath 50 is against housing proximal end 34, further advancement of advancement tool 104 through outer catheter 102 and receptacle 108 pushes pacemaker 10 out the distal opening 110 of receptacle 108.

During an implant procedure, pacemaker 10 is initially retained within receptacle 108, as shown in FIGS. 5A and 5B. The distal opening 110 of delivery tool 100 is advanced to a desired implant site. Delivery tool 100 may be advanced transvenously to deliver pacemaker 10 to an intracardiac implant site, e.g., within an atrial or ventricular chamber. It is contemplated, however, that delivery tool 100 may be tunneled subcutaneously, submuscularly, or substernally to deliver pacemaker 10 to an implant site, e.g., to an epicardial implant site or a submuscular or subcutaneous implant site. Tip electrode 42 may be exposed through distal opening 110 of receptacle 108, as shown in FIG. 5A during advancement to a test or candidate implant site. Fixation member portion 52 of retractable fixation sheath 50 is retracted. This configuration allows electrophysiological testing using tip electrode 42 at one or more test or candidate implant sites prior to deploying fixation member portion 52.

A tether 106 extends through an open lumen of advancement tool 104 and is looped around lateral rod 88 of delivery tool interface member 26. Tether 106 may be a flexible suture or wire that can be used to apply a retraction force on retractable fixation sheath 50 and pacemaker 10. In other examples, tether 106 may be a relatively stiff wire or other elongated member that may be used to apply both a pushing force for advancing retractable fixation sheath 50 and pacemaker 10 and a pulling or retraction force for retracting fixation sheath 50 as well as pulling pacemaker 10 back into receptacle 108. In some examples, tether 106 is looped around lateral rod 88 so that two free ends are exposed at the proximal end (not shown) of delivery tool 100 for applying a retraction force as needed. In some examples, tether 106 may have torsional stiffness for applying torque to delivery tool interface member 26 to cause rotation of fixation sheath 50 relative to pacemaker 10 when guide channels 58 are non-linear.

As shown in FIG. 5B, tip electrode 42 may be positioned against a tissue surface 19, e.g., the endocardial surface, to enable cardiac electrical signal sensing and/or electrical stimulation testing at a test site. For example, electrophysiological mapping may be performed by sensing cardiac electrical signals using tip electrode 42 at one or more candidate implant sites. Additionally or alternatively, a response to a pacing pulse delivered using tip electrode 42 at one or more candidate implant sites may be determined or measured. For instance, a pacing capture threshold test may be performed by delivering pacing pulses using tip electrode 42 held against cardiac tissue surface 19 by delivery tool 100 without deploying fixation member portion 52. Pressure of delivery too distal face 109 against pacemaker proximal face 35 holds tip electrode 42 at a test site without deployment of fixation member portion 52. During testing, a saline solution filling any gap or clearance between fixation sheath 50 and receptacle 108 may provide a conductive path between tip electrode 42 and housing-based electrode 24 such that tip electrode 42 and housing-based electrode 24 may be used as a cathode and anode pair during testing.

Figure 6:
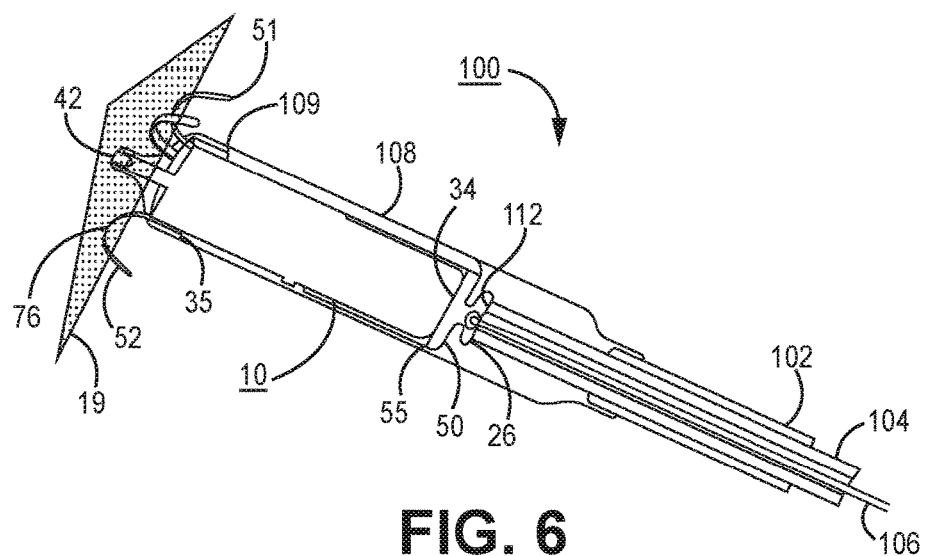
FIG. 6 is a view of the IMD and delivery tool of FIGS. 5A and 5B with the fixation sheath in a fully advanced position.

FIG. 6 is a sectional view of pacemaker 10 and delivery tool 100 with fixation sheath 50 in a fully advanced position. Pacemaker 10 is still retained within receptacle 108. After positioning tip electrode 42 at an implant site, fixation sheath 50 is advanced over housing 30 so that the tines of fixation member portion 52 are advanced through respective slots 72 forcing tine tips 51 to pierce the tissue surface 19, e.g., an endocardial surface, at the implant site. Tip electrode 42 may be held firmly against the implant site by longitudinal force applied to the outer catheter 102 during advancement of fixation sheath 50, to hold delivery tool distal face 109 against pacemaker proximal face 35.

As fixation member portion 52 is advanced further out of slots 72, tines of fixation member portion 52 regain their normally curved shape. In the fully advanced position, the inner surface of proximal end 55 of retractable fixation sheath 50 is flush against the housing proximal end 34. Tissue at the implant site is captured by the curve 76 of each tine of fixation member portion 52 as tine tips 51 curve back through the tissue at the implant site and may exit the tissue surface 19.

Figure 7:
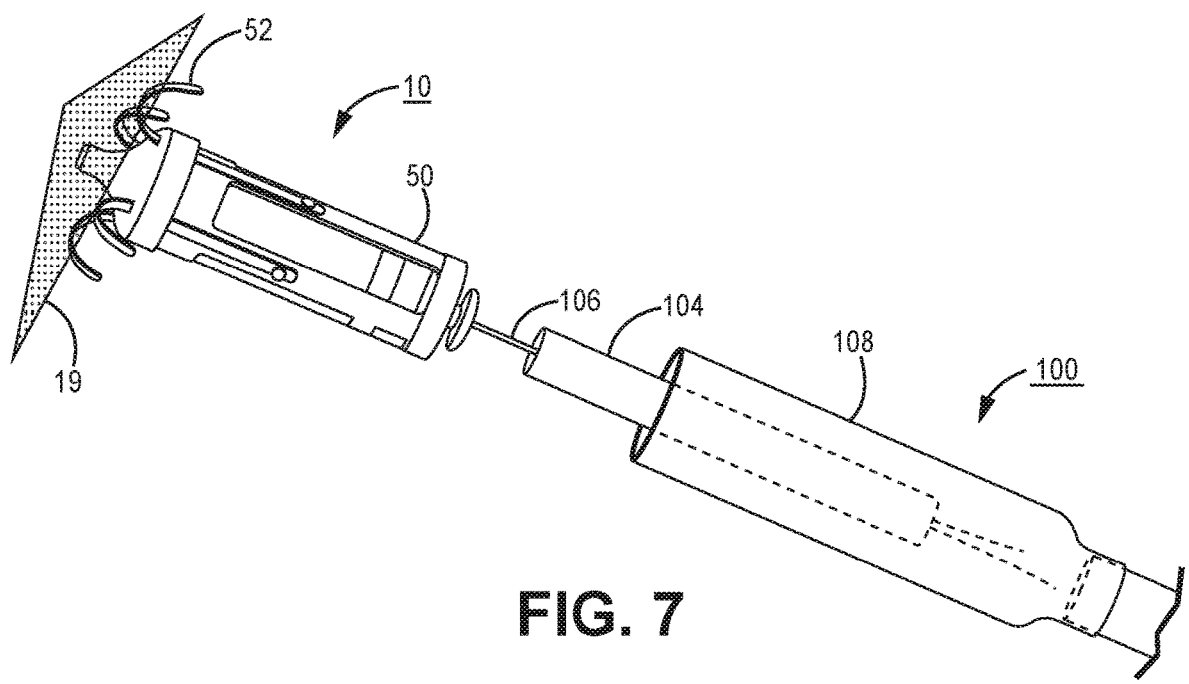
FIG. 7 is a conceptual diagram of the IMD of FIG. 6 after release from the delivery tool.

FIG. 7 is a conceptual diagram of pacemaker 10 after release from receptacle 108. Once pacemaker 10 is anchored in place at the implant site by the deployed fixation member portion 52, delivery tool 100 may be retracted to release pacemaker 10 from receptacle 108. The tether 106 may be left attached to delivery tool interface member 26 during any additional testing and confirmation of an acceptable implant site. In some cases, repositioning or removal of pacemaker 10 may be required after deployment of fixation member portion 52. Prior to removing tether 106, fixation sheath 50 may be retracted proximally over housing 30 by a pulling force applied to the proximal end of tether 106, pulling the tines of fixation member portion 52 back into slots 72 and out of the tissue surface 19. Pacemaker 10 may be guided back into receptacle 108 by retracting on tether 106. If pacemaker 10 is being moved to a different location, outer catheter 102 may be used to adjust the position of pacemaker 10 to a new implant site and fixation member portion 52 may be re-deployed by advancement of retractable fixation sheath 50 as described above. Once an acceptable implant site is confirmed, delivery tool 100 is retracted and tether 106 may be removed from delivery tool interface member 26. The entire delivery tool 100 may be withdrawn from the patient leaving pacemaker 10 implanted.

Figure 8A:
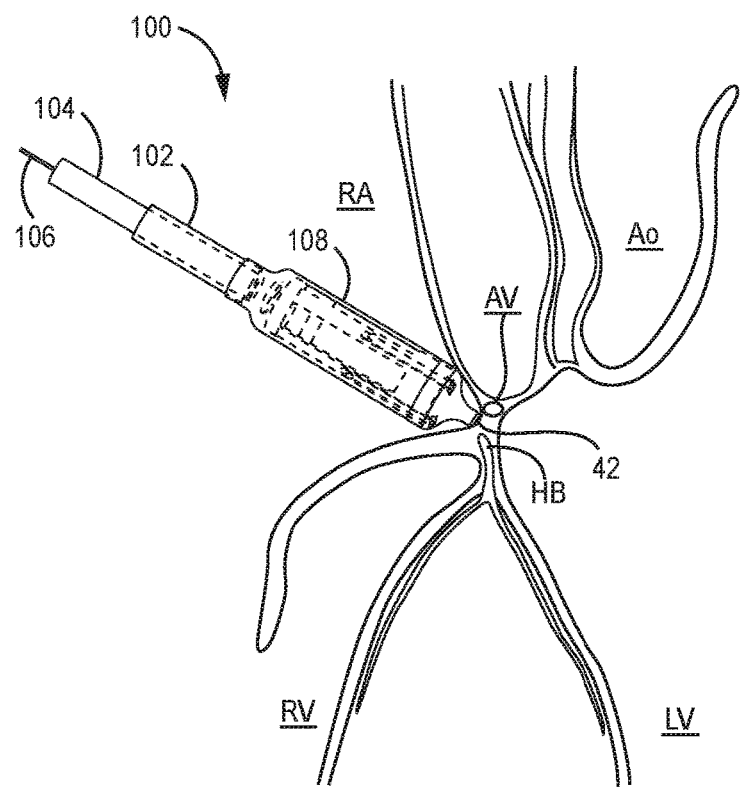
FIGS. 8A and 8B are conceptual diagrams of the IMD of FIG. 1A being implanted within the right atrium (RA) of a patient for His bundle pacing.
Figure 8B:
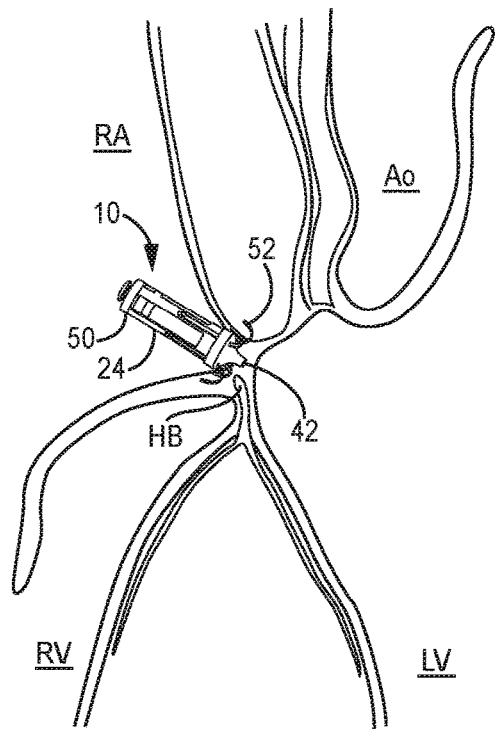

FIGS. 8A and 8B are conceptual diagrams of pacemaker 10 being implanted within the right atrium (RA) for His bundle pacing. In this example clinical application, pacemaker 10 is loaded into delivery tool 100 and advanced transvenously into the RA. Tip electrode 42 is positioned against the atrial endocardial surface or along the tricuspid valve annulus in the vicinity of the His bundle, inferior to the atrioventricular (AV) node. Electrophysiological mapping may be performed by recording a cardiac electrogram signal produced from the cardiac electrical signal received via tip electrode 42 and a return anode electrode, e.g., housing-based electrode 24.

When the cardiac electrogram signal strongly correlates to a His bundle electrogram signal, retractable fixation sheath 50 may be advanced over pacemaker housing 30 by applying longitudinal force using advancement tool 104 to deploy fixation member portion 52 and anchor pacemaker 10 in place as shown in FIG. 8B. Delivery tool 100 may be retracted and withdrawn leaving pacemaker 10 positioned for His bundle pacing via the tip electrode 42 and housing-based electrode 24 as a cathode and anode pair.

It is recognized that other electrode arrangements may be conceived and implemented with a pacemaker having a retractable and advanceable fixation sheath as disclosed herein. For example, pacemaker 10 may include one or more housing based electrodes, one or more electrodes carried by distal assembly 36, and/or one or more electrodes carried by an extension or shaft extending away from housing 30 as needed for various sensing and pacing applications.

Figure 9:
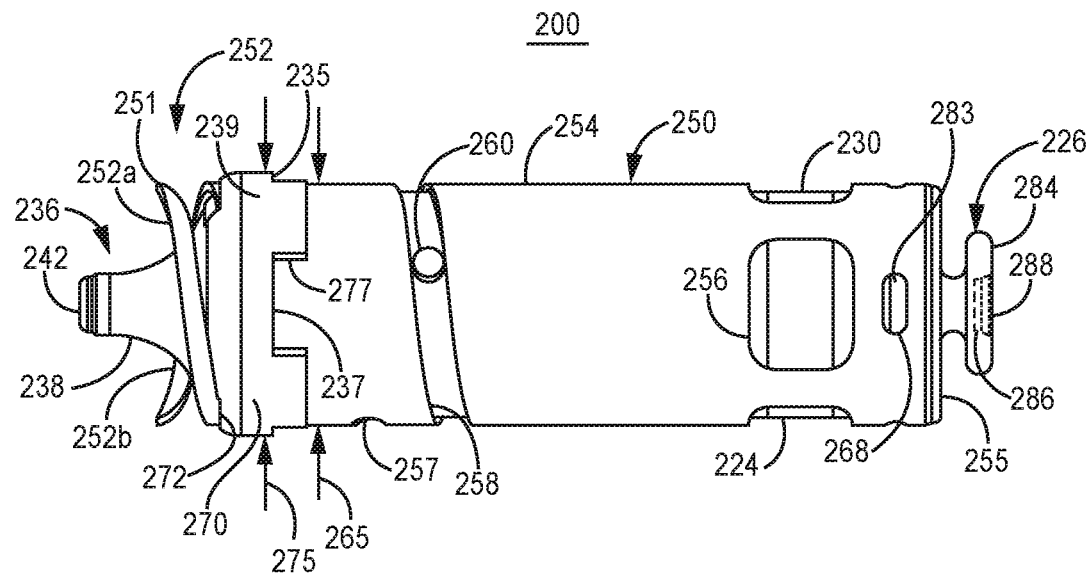
FIG. 9 is a conceptual diagram of an IMD having a retractable fixation sheath according to another example.

FIG. 9 is a conceptual diagram of pacemaker 200 having a retractable and advanceable fixation sheath 250 according to another example. Pacemaker 200 includes a housing 230, retractable fixation sheath 250, and distal assembly 236. Housing 230 defines an interior cavity that encloses electronic circuitry of pacemaker 200. Fixation sheath 250 includes a housing sheath portion 254 and a fixation member portion 252. In this example, fixation member portion 252 includes two helical fixation tines 252a and 252b each extending through a respective slot 272 passing through distal assembly 236. The slots 272 may be peripheral to a tip electrode 242 carried by distal assembly 236 such that the helical fixation tines 252a and 252b extend along a helical path near the outer circumference of distal assembly 236 and housing 230. Each helical fixation tine 252a and 252b has a tissue-piercing distal tip 251 and advances into body tissue to actively fix pacemaker 200 at an implant site upon rotation and advancement of fixation sheath 250. While two helical fixation tines 252a and 252b are shown in FIG. 9, fixation member portion 252 may include a single helical fixation tine or more than two helical fixation tines in other examples.

Fixation sheath 250 may define one or more open windows 256 for exposing a housing-based electrode 224 (and/or other sensors or therapy delivery features as needed). As generally described above, fixation sheath 250 may define multiple open windows, which may be of varying sizes and locations along housing sheath portion 254, as needed for exposing one or more housing-based electrodes, other physiological sensors, drug delivery ports, or other components of pacemaker 200 that may require an exposed surface for proper or optimal functioning. Housing sheath portion 254 may define one or more apertures 268 for receiving and retaining nubs 283 included on a circumferential surface of delivery tool interface member 226. In this way, delivery tool interface member 226 may be snapped into the proximal end of housing sheath portion 254 to thereby fixedly couple interface member 226 to housing sheath portion 254 and define a proximal end 255 of fixation sheath 250. As generally described above, medical adhesive or other bonding materials or methods may be used to fixedly couple housing sheath portion 254 and delivery tool interface member 226 in addition to, or alternatively to, the interlocking apertures 268 and nubs 283.

Housing sheath portion 254 may define one or more helical guide channels 258. The pitch of the helical guide channel 258 matches the winding pitch of the helical fixation tines 252a and 252b. Housing 230 may include at least one guide post 260 protruding laterally from housing 230 for riding within helical guide channel 258 as fixation sheath 250 is rotated relative to housing 230. In the example shown, a single guide post 260 is shown riding within a single, helical guide channel 258. In other examples, two or more guide posts may protrude from housing 230 for riding along a single, helical guide channel 258 or within each respective one of multiple helical guide channels. Guide channel 258 has a distal end 257 that may act as a mechanical stop against post 260 to prevent over-retraction of fixation sheath 250. Proximal end 255 of fixation sheath 250 may act as a mechanical stop that prevents over-advancement of fixation sheath 250 by interfacing with the proximal end 234 (shown in FIG. 10) of housing 230 during rotational advancement of fixation sheath 250 relative to housing 230.

As described below in conjunction with FIGS. 13A-C, a delivery tool may be used to engage with delivery tool interface member 226 for applying torque to rotate retractable fixation sheath 250 relative to housing 230 and distal assembly 236. Fixation sheath 250 is advanced relative to housing 230 by rotating and advancing the helical guide channel 258 along the guide post 260. In some examples, delivery tool interface member 226 includes a head 284 having a recess 286 in which a lateral rod 288 is mounted. The delivery tool may include a tether that can be removably coupled to rod 288. The tether may have torsional stiffness for transferring torque applied at its proximal end to delivery tool interface member 226 to cause rotation of retractable fixation sheath 250. In other examples, the delivery tool may include an advancement tool configured to be removably coupled to head 284 for applying torque to cause rotation of retractable fixation sheath 250.

Pacemaker 200 includes distal assembly 236 having a molded or machined body 270 defining a distal surface 238 and a circumferential surface 239. Body 270 may be formed from two or more components, for example an inner body and outer ring, that are assembled together and fixedly joined by medical adhesive or other joining methods. The outer diameter 275 of circumferential surface 239, or at least a portion thereof, may be greater than the outer diameter 265 of retractable fixation sheath 250 to define a proximal face 235 of body 270. As described below, a distal face of a delivery tool may be configured to mate with proximal face 235 for applying a longitudinal force for advancing pacemaker 200 to a test or implant site. Proximal face 235 may be a toothed or notched face, including one or more notches 237 as shown defining side faces 277. A distal face of the delivery tool may interlock with the notched proximal face 235 to resist rotation of distal assembly 236 and housing 230 coupled thereto during rotation of retractable fixation sheath 250.

Figure 10:
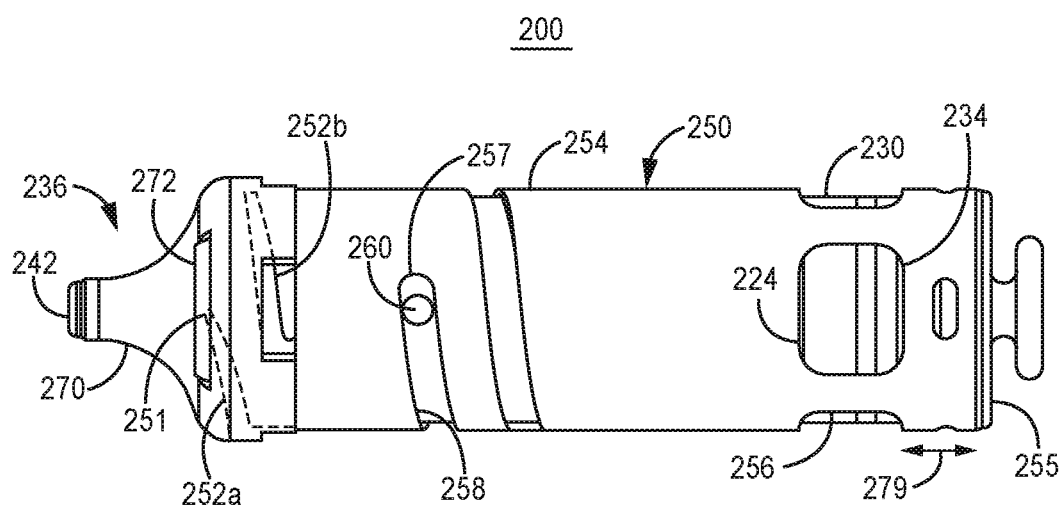
FIG. 10 is a conceptual diagram of the IMD of FIG. 9 with the fixation sheath in a fully retracted position.

FIG. 10 is a conceptual diagram of pacemaker 200 with fixation sheath 250 in a fully retracted position. Fixation sheath 250 has been rotated and retracted relative to housing 230 such that guide post 260 has advanced toward (or all the way to) the distal end 257 of helical guide channel 258. Fixation member portion 252 is retracted within distal assembly 236 such that helical fixation tines 252a and 252b extend alongside housing 30 and/or within distal assembly slots 272. In the fully retracted position of fixation sheath 250, the distal tip 251 of each helical fixation tine 252a and 252b may reside just within a respective slot 272 of distal assembly body 270. The housing proximal end 234 is spaced apart from the fixation sheath proximal end 255 by a gap 279 corresponding to the longitudinal distance that retractable fixation sheath 250 traverses when rotationally advanced from the fully retracted position shown in FIG. 10 to the fully advanced position shown in FIG. 9.

The housing-based electrode 224 may be unexposed or partially exposed by windows 256 in the fully retracted position. Testing using tip electrode 242 and housing-based electrode 224 may be performed with retractable fixation sheath 250 in the fully retracted position without injuring tissue at the test site by keeping helical fixation member tines 252a and 252b within the slots 272 of distal assembly 236. In some cases, the inner diameter of housing sheath portion 254 may be sized to allow a small clearance gap between the inner diameter of housing sheath portion 254 and housing 230, which may be filled with saline or bodily fluid during electrophysiological testing providing a conductive path between tip electrode 242 and housing-based electrode 224.

Figure 11:
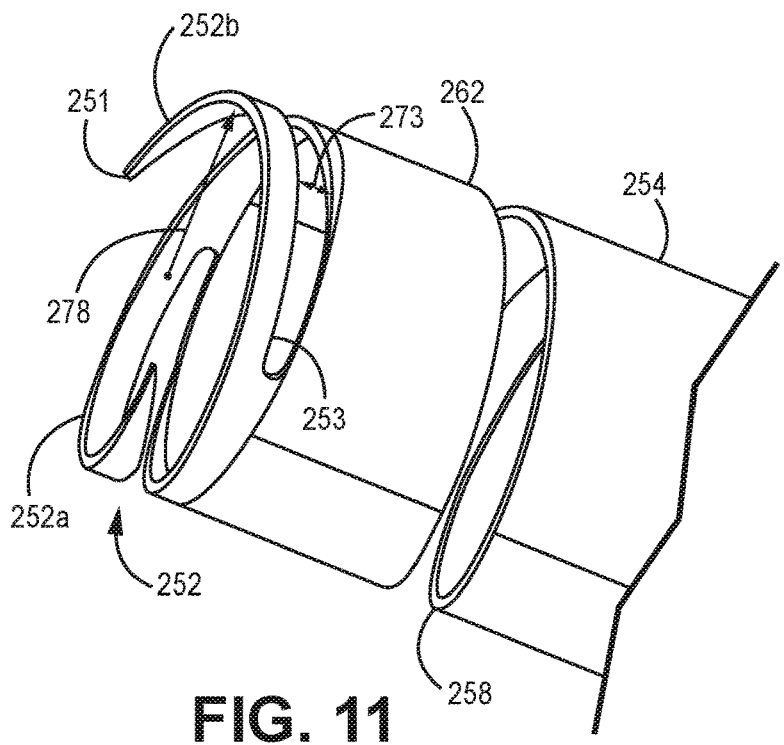
FIG. 11 is an enlarged view of a distal portion of the fixation sheath of FIG. 9.

FIG. 11 is an enlarged view of a distal portion of retractable fixation sheath 200. The helical tines 252a and 252b of fixation member portion 252 may each extend from a fixed end 253 attached to a circumferential distal ring 262 of housing sheath portion 254 to a free distal tip 251. Helical tines 252a and 252b may have a fixed radius 278, e.g., equal to the radius of housing sheath portion 254. In other examples, the helical tines 252a and 252b may have a variable radius that progressively increases or decreases between fixed end 253 and free distal tip 251. The pitch of guide channel 258 matches the pitch of helical fixation tines 252a and 252b so that as fixation sheath 250 is rotated relative to the pacemaker housing 230 as controlled by the interaction of housing guide posts 260 (shown in FIG. 10) and guide channels 258, helical fixation tines 252a and 252b are rotated a controlled depth into tissue at the implant site. The helical arc length of guide channel 258 may be at least equal to or greater than the arc length from free distal tip 251 to the fixed end 253 of each helical tine 252a and 252b such that rotation of fixation sheath 250 to the fully advanced position as shown in FIG. 9 allows full extension of the helical tines 252a and 252b from the respective distal assembly slots 272 (shown in FIG. 9). The arc length of guide channel 258 may be selected to limit the total distance that helical tines 252a and 252b can be advanced out of their respective slots 272 and therefore limit the depth of distal tips 251 into the tissue at the implant site.

The helical fixation tines 252a and 252b are spaced apart from distal circumferential ring 262 by a gap 273 that is sized as needed to enable helical fixation tines 252a and 252b to clear distal assembly 236 as distal tips 251 are advanced out of slots 272. The gap 273 may be sized relatively larger to accommodate the dimensions of the distal assembly 236, for example, by including a longitudinal beam extending between and joining circumferential ring 262 and the fixed end 253.

Figure 12:
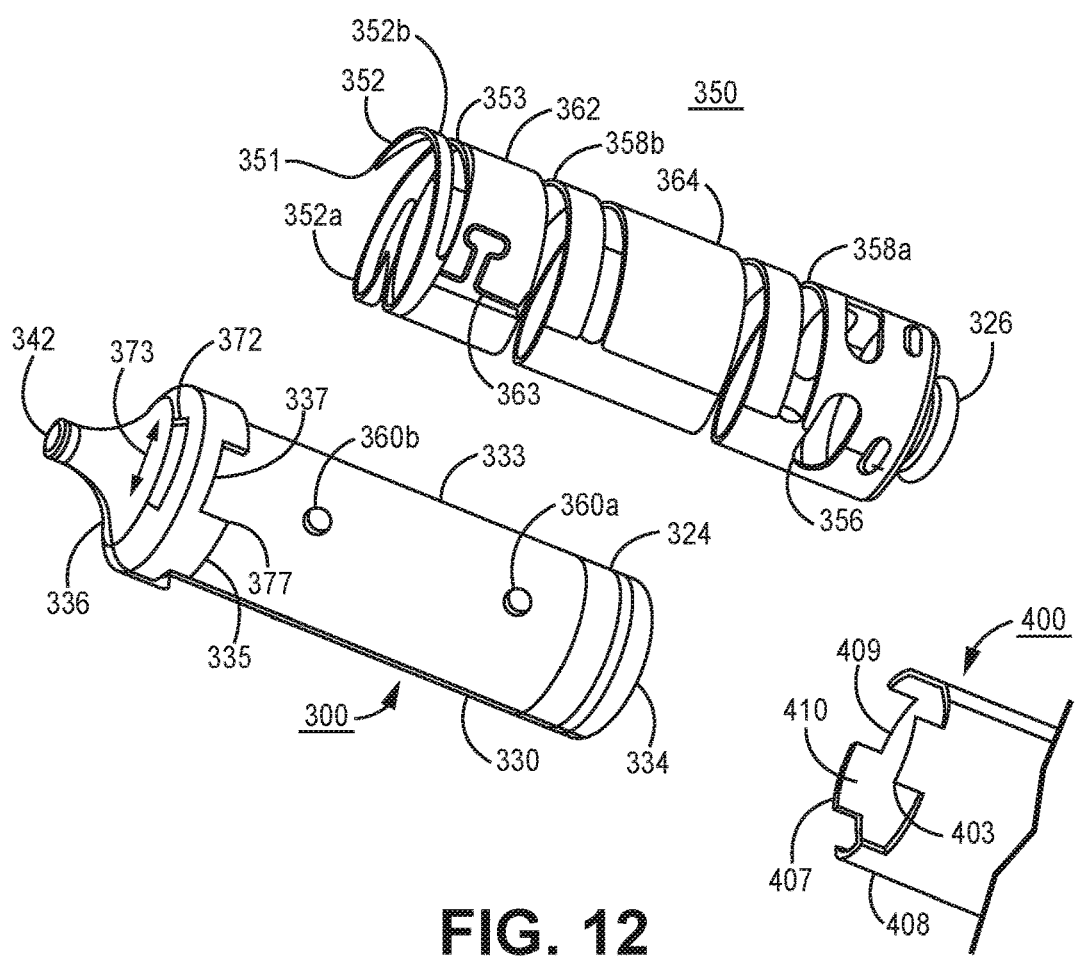
FIG. 12 is a perspective view of an IMD system including an IMD, an advanceable fixation sheath, and a delivery tool according to another example.

FIG. 12 is a perspective view of a pacemaker 300, retractable fixation sheath 350, and a distal portion of a delivery tool 400 according to another example. Fixation sheath 350 includes a fixation member portion 352 and housing sheath portion 354. In this example, housing sheath portion 354 includes longitudinal sidewall 364 defining two helical guide channels, a proximal guide channel 358a and a distal guide channel 358b for receiving and riding along corresponding proximal and distal posts 360a and 360b, respectively, of pacemaker housing 330. The pitch of guide channels 358a and 358b matches the pitch of helical fixation tines 352a and 352b to allow controlled deployment of helical fixation tines 352a and 352b into tissue at the implant site as retractable fixation sheath 350 is rotated and advanced over pacemaker housing 330.

Pacemaker 300 includes a housing 330 having a proximal end 334, and a distal assembly 336 and outer sidewall 333 extending there between. The distal assembly 336 includes a slot 372 corresponding to each helical fixation tine 352a and 352b, through which the distal tips 351 of the fixation tines are threaded through during assembly of retractable fixation sheath 350 onto housing 330. The width 373 of each slot 372 is provided wide enough to allow clearance of the fixation tined 352a and 352b to be rotationally advanced out from the respective slot 372 a desired distance without interference between the tines 352a and 352b and the distal assembly 336 and enable penetration of tines 352a and 352b into the cardiac tissue at the implant site to a desired depth.

Housing 330 includes posts 360b and 360a or other radially protruding guide members for engaging with respective guide channels 358a and 358b and guiding advancement of fixation sheath 350 as it is rotated with respect to housing 330. Fixation sheath 350 may be assembled onto pacemaker housing 330 by sliding the fixation member portion 352 over housing proximal end 334 and advancing sheath 350 forward until posts 360a and 360b are received within respective guide channels 358a and 358b. In some examples, fixation sheath 350 may flex over posts 360a and 360b and elastically regain its cylindrical shape. In other examples, posts 360a and 360b may be coupled to housing outer sidewall 333 after advancing sheath 350 over housing 330. For example posts 360a and 360b may be welded or press fit onto housing outer sidewall 333.

In still other examples, sheath 350 may include one or more stress-relieving features 363 to allow distal circumferential ring 362 to flexibly expand as it is passed over posts 360a and 360b and regain its cylindrical shape alongside housing outer sidewall 333 with posts 360a and 360b in alignment with guide channels 358a and 358b. In the example shown, stress-relieving feature 363 is shown as a slot that is cut through distal circumferential ring 362, extending from the distal end 353 of housing sheath portion 354 to the distal guide channel 358b. The cut may have a peg shape as shown, which allows outward expansion of the distal circumferential ring 362 without losing the integrity of the distal circumferential ring, still fully circumscribing housing 330. The cut may have a width corresponding to the circumferential expansion needed to pass distal circumferential ring 362 over guide posts 360a and 360b as fixation sheath 350 is assembled onto housing 330 by advancement over housing proximal end 334.

Housing 330 may include a housing-based electrode 324 positioned near housing proximal end 334 (or other locations along housing 330) that is exposed by window(s) 356 defined by housing sheath portion 354. In other examples, one or more housing-based electrodes may be carried by distal assembly 336 and/or housing 330.

Distal assembly 336 has a proximal face 335, which may be a notched face including one or more notches 337 having side faces 377 as shown. The delivery tool 400 includes a receptacle 408 having an open distal end 410 through which pacemaker 300 is received after retractable fixation sheath 350 is assembled onto pacemaker housing 330. Receptacle 408 defines a distal face 409 configured to mate with proximal face 335 of distal assembly 336. Tabs 407 of receptacle 408 mate with notches 337 of distal assembly 336 such that side faces 377 of distal assembly 336 defined by notches 337 and side faces 403 of receptacle 408 defined by tabs 407 interfere with each other during rotation of retractable fixation sheath 350. Interference between side faces 403 and 377 prevents rotation of pacemaker 300 during rotation of fixation sheath 350 when a counter-torque is applied at the proximal end (not shown in FIG. 12) of delivery tool 400 as torque is applied to delivery tool interface member 326 to cause rotation of fixation sheath 350.

Figure 13A:
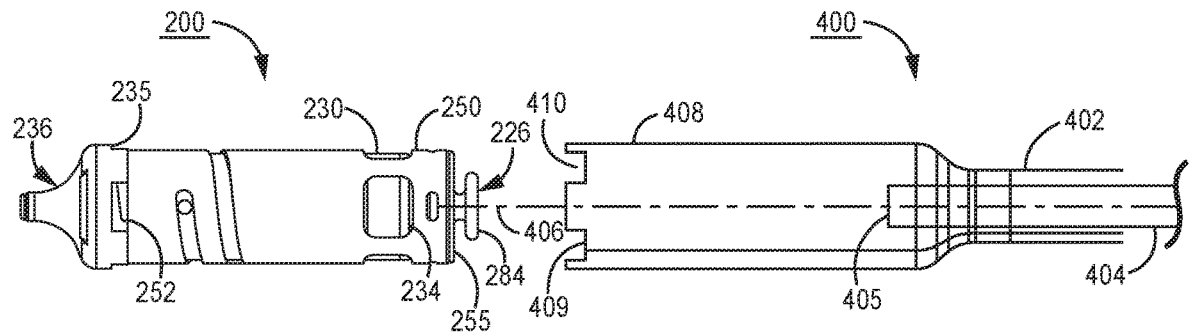
FIG. 13A is a plan view of the IMD of FIG. 9 and a delivery tool.

FIG. 13A is a plan view of pacemaker 200 of FIG. 9 and a delivery tool 400. Delivery tool 400 may include an outer catheter 402, advancement tool 404 and tether 406. Outer catheter 402 includes receptacle 408 at its distal end, defining distal opening 410 and notched distal face 409 configured to mate with the corresponding notched proximal face 235 of pacemaker distal assembly 236. Pacemaker 200 may be loaded into receptacle 408 through open distal end 410 with fixation sheath 250 in a fully retracted position. Fixation member portion 252 is retracted within distal assembly 236 and/or alongside housing 230 and housing proximal end 234 is spaced apart from fixation sheath proximal end 255. The notched distal face 409 of tool 400 is aligned and mated with the notched proximal face 235 of pacemaker 200.

Outer catheter 402 has an open lumen through which an elongated, tubular advancement tool 404 may extend. Tether 406 may extend through an open lumen of advancement tool 404 and is configured to be removably coupled to delivery tool interface member 226. Tether 406 may be a flexible elongated member, e.g., a suture or flexible wire, that may be used to pull retractable fixation sheath 250 into the retracted position and/or pull pacemaker 200 into receptacle 408.

In some examples, tether 406 may have torsional resistance such that torque applied by a user at the proximal end (not shown) of tether 406 is transferred to the head 284 of delivery tool interface member 226 to cause rotation of fixation sheath 250. Tether 406 may be configured to attach to proximal head 284, e.g., by looping around a lateral rod extending with in a recess of proximal head 284 as shown in FIG. 4, for rotating retractable fixation sheath 250. Rotation of the proximal end (not shown) of tether 406 by a user may cause rotation of retractable fixation sheath 250 relative to housing 230.

In the example shown, clockwise rotation of the proximal end of tether 406 rotates fixation sheath 250 clockwise to cause advancement of fixation sheath 250 relative to housing 230 and deployment of fixation member portion 252. Counter-clockwise rotation of the proximal end of tether 406 by a user causes retraction of fixation sheath 250. In some examples, tether 406 may possess longitudinal compressive strength such that longitudinal force may be transferred from the tether proximal end to the tether distal end for applying longitudinal force against delivery tool interface member 226 during forward rotation of fixation sheath 250 and/or pushing against delivery tool interface member 226 for pushing pacemaker 200 out of receptacle 408 after deployment of fixation member portion 252, as outer catheter 402 is withdrawn.

Advancement tool 404 may define a distal pushing surface 405 that is sized to interface with delivery tool interface member 226 for pushing pacemaker 200 out of receptacle 408 after fixation of pacemaker 200 at an implant site. Distal pushing surface 405 may be a circumferential surface defined by the wall thickness of advancement tool 404. In other examples, advancement tool 404 may include a pusher cone or cup that conforms to delivery tool interface member 226, e.g., for removably engaging with head 284, for rotatably advancing and retracting fixation sheath 250 and/or for pushing and pulling pacemaker 200 out of and into receptacle 408.

Interference between notched proximal face 235 of distal assembly 236 and notched distal face 409 of receptacle 408 prevents rotation of distal assembly 236 and housing 230 during rotation of fixation sheath 250. A user may hold the proximal end of outer catheter 402, having adequate torsional strength to prevent rotation of the receptacle 408 when fixation sheath 250 is rotated. In other examples, tether 406 and/or advancement tool 404 may be used to resist rotation of fixation sheath 250 while distal assembly 236 (and housing 230 attached thereto) is rotated by rotating outer catheter 402 at its proximal end. Rotational force may be applied to distal assembly 236 through the interaction of notched distal face 409 of receptacle 408 and notched proximal face 235 of distal assembly 236. If rotation of retractable fixation sheath 250 is resisted during rotation of distal assembly 236, housing 230 may be retracted proximally into retractable fixation sheath 250, causing deployment of fixation member portion out of slots 272 of distal assembly 236. When housing 230 is rotated in an opposite direction relative to fixation sheath 250, housing 230 may be advanced distally within fixation sheath 250 causing fixation member portion 252 to be retracted within distal assembly 236. It is recognized that numerous configurations of delivery tool 400 and corresponding features of pacemaker 200 for mating or interfacing with delivery tool 400 may be conceived that enable rotation of either (or both of) fixation sheath 250 or housing 230 relative to the other to cause longitudinal translation of fixation sheath 250 relative to pacemaker housing 230 and distal assembly 236 to thereby deploy (or retract) fixation member portion 252.

Figure 13B:
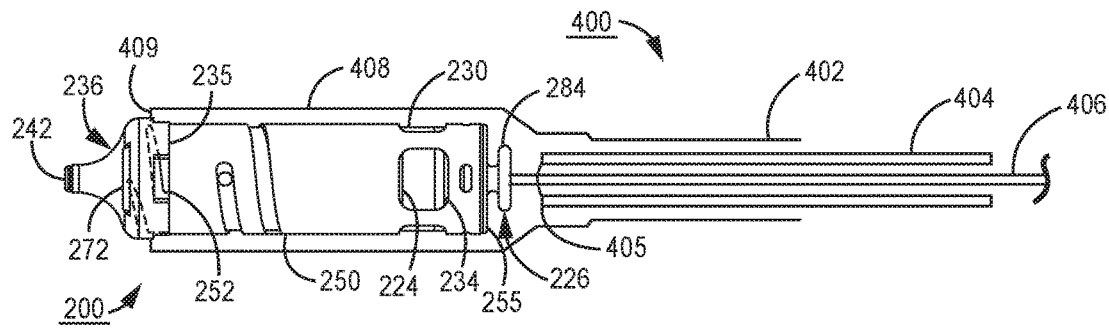
FIG. 13B is a view of the IMD of FIG. 9 loaded into a receptacle of the delivery tool of FIG. 13A.

FIG. 13B is a view of pacemaker 200 loaded into receptacle 408 of delivery tool 400. Retractable fixation sheath 250 is in the fully retracted position. Tether 406 may be used to maintain tension in the proximal direction on delivery tool interface member 226 to maintain retractable fixation sheath 250 in the retracted position. The distal face 409 of outer catheter 402 may be used to hold distal assembly, and tip electrode 242, at an electrophysiological mapping, testing or candidate implant site. In this configuration, electrophysiological mapping, pacing capture threshold testing, or other electrophysiological testing, signal recording or measurements may be performed using tip electrode 242 and housing-based electrode 224, without deploying fixation member portion 252. In other examples, a housing-based electrode may be carried by distal assembly 236, proximal to tip electrode 242, for use during testing or measurements. In some examples, distal assembly 236 may carry other sensors for measuring or recording physiological signals.

Figure 13C:
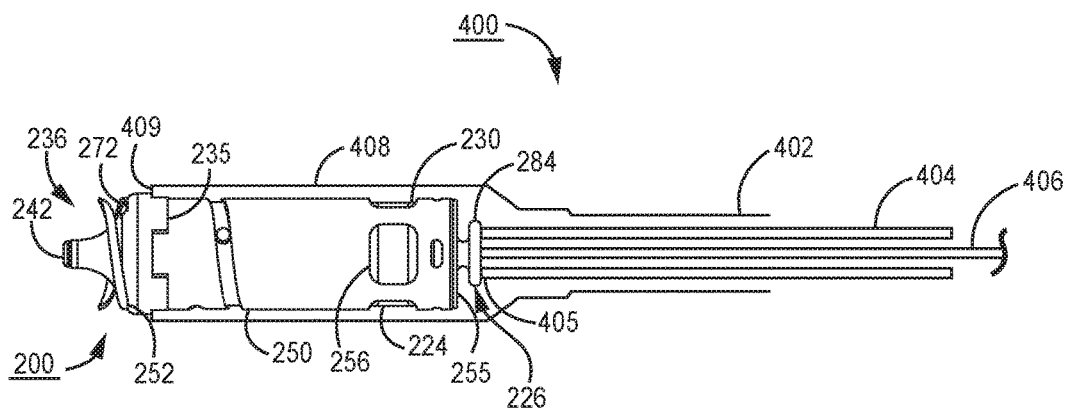
FIG. 13C is a view of the IMD of FIG. 9 loaded into the receptacle of the delivery tool of FIG. 13A with the fixation sheath in the fully advanced position.

FIG. 13C is a view of pacemaker 200 loaded into receptacle 408 of delivery tool 400 with fixation sheath 250 in the fully advanced position. Tether 406 may be configured to engage a portion of the head 284 of delivery tool interface member 226 as described above. Torque applied to the proximal end of tether 406 may be transferred to delivery tool interface member 226 to cause rotation of fixation sheath 250, thereby advancing fixation sheath 250 to deploy fixation member portion 252. Tines of fixation member portion 252 may exit the slots 272 of distal assembly 236 and pierce an adjacent body tissue, e.g., the endocardial surface of an atrial or ventricular heart chamber. Upon full advancement of fixation sheath 250, fixation member portion 252 rotates into tissue at the implant site, actively fixing pacemaker 200 at the implant site. Advancement tool 404 may be used to push pacemaker 200 out of receptacle 408 as outer catheter 402 is withdrawn from pacemaker 200. Tether 406 may be removed from delivery tool interface member 226 after any final testing at the implant location. Delivery tool 400 may be removed leaving pacemaker 200 in place.

Figure 14:
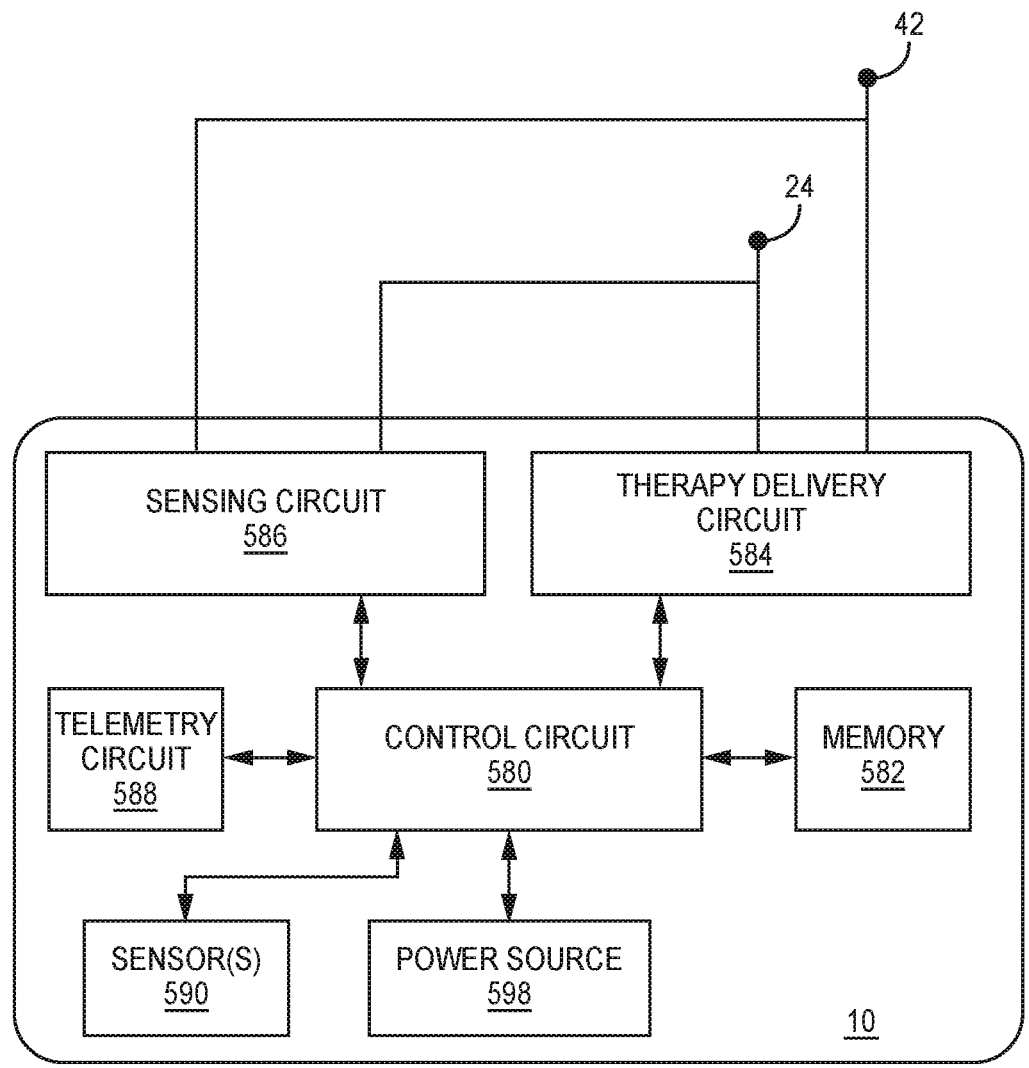
FIG. 14 is a block diagram of circuitry that may be enclosed within the housing of an IMD having a retractable fixation sheath according to one example.

FIG. 14 is a block diagram of circuitry that may be enclosed within the housing 30 of pacemaker 10 (or any of the other examples of pacemakers shown in the accompanying drawings). The electronic circuitry enclosed within housing 30 includes software, firmware and hardware that cooperatively monitor cardiac electrical signals, determine when a pacing therapy is necessary, and deliver electrical pacing pulses to the patient's heart as needed according to programmed pacing mode and pacing pulse control parameters. The electronic circuitry includes a control circuit 580, memory 582, therapy delivery circuit 584, sensing circuit 586, and telemetry circuit 588. In some examples, pacemaker 10 includes one or more sensors 590 for producing a signal that is correlated to a physiological function, state or condition of the patient, such as a patient activity sensor, for use in determining a need for pacing therapy and/or controlling a pacing rate.

A power source 598 provides power to the circuitry of pacemaker 10 including each of the components 580, 582, 584, 586, 588 and 590 as needed. Power source 598 may include one or more energy storage devices, such as one or more rechargeable or non-rechargeable batteries. The connections between power source 598 and each of the other components 580, 582, 584, 586, 588 and 590 are to be understood from the general block diagram of FIG. 14, but are not shown for the sake of clarity. For example, power source 598 is coupled to one or more charging circuits included in therapy delivery circuit 584 for providing the power needed to charge holding capacitors included in therapy delivery circuit 584 that are discharged at appropriate times under the control of control circuit 580 for delivering pacing pulses according to a programmed pacing mode. Power source 598 is also coupled to components of sensing circuit 586, such as sense amplifiers, analog-to-digital converters, switching circuitry, etc., sensors 590, telemetry circuit 588 and memory 582 to provide power to the various circuits as needed.

The functional blocks shown in FIG. 14 represent functionality included in pacemaker 10 and may include any discrete and/or integrated electronic circuit components that implement analog and/or digital circuits capable of producing the functions attributed to pacemaker 10 herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the pacemaker and by the particular detection and therapy delivery methodologies employed by the pacemaker. Providing software, hardware, and/or firmware to accomplish the described functionality in the context of any modern cardiac medical device system, given the disclosure herein, is within the abilities of one of skill in the art.

Memory 582 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 582 may include non-transitory computer readable media storing instructions that, when executed by one or more processing circuits, cause control circuit 580 and/or other circuits to perform pacing function or other sensing and therapy delivery functions attributed to pacemaker 10. The non-transitory computer-readable media storing the instructions may include any of the media listed above.

Control circuit 580 communicates, e.g., via a data bus, with therapy delivery circuit 584 and sensing circuit 586 for sensing cardiac electrical signals and controlling delivery of cardiac electrical stimulation therapies in response to sensed cardiac events, e.g., P-waves and/or R-waves, or the absence thereof. Tip electrode 42 and proximal housing-based electrode 24 may be electrically coupled to therapy delivery circuit 584 for delivering electrical stimulation pulses to the patient's heart and coupled to sensing circuit 586 for sensing cardiac electrical signals. In other examples, pacemaker 10 may include three or more electrodes coupled to therapy delivery circuit and/or sensing circuit. Therapy delivery circuit 584 may include one or more pacing channels configured for delivering pacing pulses via one or more respective pacing electrode vectors. Sensing circuit 586 may include one or more sensing channels configured for receiving one or more cardiac electrical signals via respective sensing electrode vectors.

Sensing circuit 586 may be configured to amplify, filter, digitize and rectify the cardiac electrical signal received from the electrodes 42 and 24 to improve the signal quality for detecting cardiac electrical events. The cardiac event detection circuitry may include one or more sense amplifiers, filters, rectifiers, threshold detectors, comparators, analog-to-digital converters (ADCs), timers or other analog or digital components. A cardiac event sensing threshold, e.g., a P-wave sensing threshold or an R-wave sensing threshold, may be automatically adjusted under the control of control circuit 580, e.g., based on timing intervals and sensing threshold values determined by control circuit 580, stored in memory 582, and/or controlled by hardware, firmware and/or software of control circuit 580 and/or sensing circuit 586.

Upon detecting a cardiac electrical event based on a sensing threshold crossing, sensing circuit 586 may produce a sensed event signal that is passed to control circuit 580. For example, atrial sensing circuit 586 may produce a P-wave sensed event signal in response to a P-wave sensing threshold crossing or an R-wave sensed event signal in response to an R-wave sensing threshold crossing. The sensed event signals are used by control circuit 580 for setting one or more pacing escape interval timers that control the basic time intervals used for scheduling cardiac pacing pulses. A sensed event signal may trigger or inhibit a pacing pulse depending on the particular programmed pacing mode.

In some examples, pacemaker 10 may be configured to deliver a variety of pacing therapies including bradycardia pacing, cardiac resynchronization therapy, post-shock pacing, and/or anti-tachycardia pacing. Therapy delivery circuit 584 includes charging circuitry, one or more charge storage devices such as one or more holding capacitors coupled to the charging circuitry, an output capacitor, and switching circuitry that controls when the holding capacitor(s) are charged and discharged across the output capacitor to deliver a pacing pulse via tip electrode 42 and proximal housing-based electrode 24. Charging of a holding capacitor of therapy delivery circuit 584 to a programmed pacing voltage amplitude and discharging of the capacitor for a programmed pacing pulse width may be performed by therapy delivery circuit 584 according to control signals received from control circuit 580. For example, a pace timing circuit included in control circuit 580 may include programmable digital counters set by a microprocessor of the control circuit 580 for controlling the basic pacing time intervals associated with a particular pacing mode or therapy. The microprocessor of control circuit 580 may also set the amplitude, pulse width, polarity or other characteristics of the cardiac pacing pulses, which may be based on programmed values stored in memory 582.

Pacemaker 10 may include other sensors 590 for sensing signals from the patient for use in determining a need for and/or controlling electrical stimulation therapies delivered by therapy delivery circuit 584. In some examples, a sensor indicative of a need for increased cardiac output may include a patient activity sensor, such as an accelerometer. An increase in the metabolic demand of the patient due to increased activity as indicated by the patient activity sensor may be determined by control circuit 580 for use in determining a sensor-indicated pacing rate.

Control parameters utilized by control circuit 580 for sensing cardiac events, and controlling pacing therapy delivery may be programmed into memory 582 via telemetry circuit 588. Telemetry circuit 588 includes a transceiver and antenna for communicating with an external device such as a programmer or home monitor, using radio frequency communication or other communication protocols. Under the control of control circuit 580, telemetry circuit 588 may receive downlink telemetry from and send uplink telemetry to the external device. In some cases, telemetry circuit 588 may be used to transmit and receive communication signals to/from another medical device implanted in the patient.

When pacemaker 10 is retained within a delivery tool with fixation sheath 50 in the retracted position, a clinician or other user may interact with pacemaker 10 using an external programmer in telemetric communication with telemetry circuit 588. Commands may be transmitted to pacemaker 10 to cause pacemaker 10 to deliver pacing pulses, for example for conducting a pacing capture threshold test, measuring pacing impedance, or performing other tests to determine a pacing or therapy response. Cardiac electrical signals received by sensing circuit 586 as pacemaker 10 is moved to various test sites using a delivery tool may be transmitted to an external device via telemetry circuit 588 for observation and review by a clinician or for automated, computerized electrophysiological analysis.

After identifying an implant site based on the cardiac response to test pacing pulses and/or electrophysiological mapping, the retractable fixation sheath 50 may be advanced to deploy the fixation member portion and actively fix the pacemaker 10 at the implant site. If pacemaker 10 needs to be removed or relocated, the fixation sheath 50 may be retracted to withdraw the fixation member portion from cardiac tissue.

Figure 15:
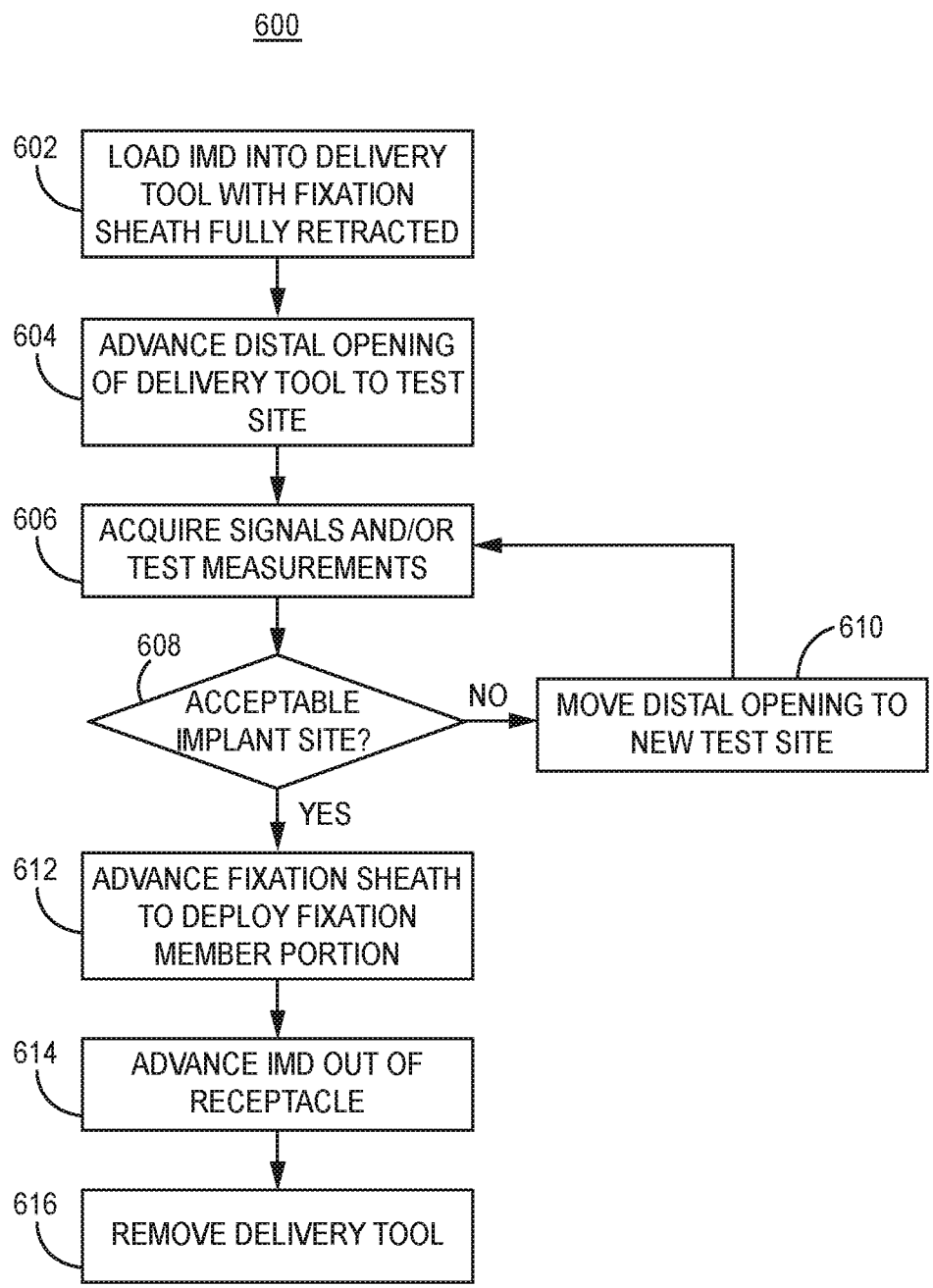
FIG. 15 is a flow chart of a method for using an IMD having a retractable fixation sheath according to one example.

FIG. 15 is a flow chart 600 of a method for using an IMD having a retractable fixation sheath according to one example. At block 602, the IMD, e.g., pacemaker 10 of FIG. 1A or any of the other examples of pacemakers presented herein, may be loaded into a receptacle of a delivery tool. At block 604, a distal opening of the delivery tool is advanced internally to a patient's body along an implant pathway to a test site. A distal assembly of the IMD including one or more electrodes and/or or other sensor(s) as generally described herein extends from the delivery tool distal opening and is positioned at the test site for acquiring a physiological signal and or obtaining one or more test measurements at block 606. For example, electrophysiological mapping and/or pacing capture thresholds or other electrical stimulation response measurements may be obtained at block 606.

If the test site is not an acceptable implant site, as determined at block 608 based on the acquired signals and/or test measurements, the distal opening of the delivery tool may be relocated to a new test site at block 610 for positioning the distal assembly of the IMD at the new test site for acquiring new signals and or test measurements at the new test site at block 606. In some examples, electrophysiological mapping is performed at multiple test sites before selecting an implant site.

If all desired measurements or signals have been obtained and the test site is an acceptable implant site, as determined at block 608 based on the acquired signals and/or test measurements, the delivery tool is used to advance the fixation sheath to deploy the fixation member portion at block 612. The IMD is anchored at the selected implant site by the deployed fixation member portion. The delivery tool may then be used to advance the IMD out of the receptacle at block 614, e.g., by pushing against a delivery tool interface member of the IMD while the receptacle is withdrawn from the IMD. Any final testing may be performed before removing the delivery tool from the pacemaker. For example, the IMD may remain tethered to the delivery tool until final verification of an acceptable implant site. At bock 616, the delivery tool is removed from the patient's body leaving the IMD anchored at the implant site by the fixation sheath in the fully advanced position.

Thus, an IMD having a fixation sheath that is advanceable and retractable relative to the IMD housing has been presented in the foregoing description with reference to specific embodiments. It is to be understood that various aspects presented in the drawings and corresponding description may be combined in other combinations than the specific embodiments presented here. It is appreciated that various modifications to the referenced embodiments may be made without departing from the scope of the disclosure and the following claims.

What is claimed is:

1. An implantable medical device comprising:
a housing enclosing electronic circuitry of the implantable medical device, the housing having a proximal end, a distal end and an outer sidewall extending from the proximal end to the distal end;
a fixation sheath comprising a housing sheath portion and a fixation member portion that extends from the housing sheath portion, wherein the housing sheath portion is advanceable from a first position to a second position along the outer sidewall of the housing, the fixation member portion being retracted toward the proximal end of the housing in the first position and deployed to extend away from the distal end of the housing in the second position for anchoring the implantable medical device at an implant site; and
a delivery tool interface member comprising:
a flange extending proximally from the housing sheath portion; and
a head extending proximally from a proximal end of the flange and defining an axial recess disposed in a proximal surface of the head, wherein the head comprises a lateral rod extending across the axial recess, wherein the flange or the head define a surface configured to interface with a pushing surface of a delivery tool for advancing the housing sheath portion from the first position to the second position, and wherein the axial recess is configured to receive a tether of the delivery tool for retracting, by the lateral rod, the housing sheath portion from the second position to the first position.

2. The device of claim 1, wherein the housing sheath portion circumscribes at least a portion of the outer sidewall of the housing.

3. The implantable medical device of claim 1, further comprising:
at least one housing-based sensor,
wherein the fixation sheath comprises at least one window exposing the at least one housing-based sensor.

4. The implantable medical device of claim 1, wherein:
the housing comprises a guide member protruding outward from the outer sidewall of the housing; and
the housing sheath portion comprises a guide channel for receiving the guide member, the guide channel configured to slide along the guide member during advancement of the housing sheath portion from the first position to the second position.

5. The implantable medical device of claim 4, wherein the guide channel is non-linear.

6. The implantable medical device of claim 4, wherein:
the fixation member portion comprises at least one helical tine having a winding pitch;
the guide channel is a helical guide channel having a pitch corresponding to the winding pitch of the helical tine; and
the housing sheath portion is advanceable from the first position to the second position by rotating the housing sheath portion relative to the housing such that the helical guide channel slides along the guide member.

7. The implantable medical device of claim 4, wherein the guide channel comprises a distal end defining a stop for interfacing with the guide member to prevent over-retraction of the fixation sheath relative to the housing.

8. The implantable medical device of claim 1, wherein the fixation sheath comprises a proximal end that interfaces with the proximal end of the housing in the second position of the housing sheath portion.

9. The implantable medical device of claim 1, further comprising:
a distal assembly comprising a body coupled to the housing distal end and having at least one slot extending through the body;
the fixation member portion comprising at least one tine having a distal tip, the at least one tine being retracted within a slot of the distal assembly in the first position and extended out of the slot in the second position.

10. The implantable medical device of claim 1, wherein the fixation member portion comprises a plurality of tines that are elastically deformable from a normally curved position when located in the second position to an extended position alongside the outer sidewall of the housing when located in first position.

11. The implantable medical device of claim 1, further comprising a distal assembly comprising a body coupled to the housing distal end and having a proximal face configured to interface with a distal face of a delivery tool for advancing the implantable medical device to an implant site.

12. The implantable medical device of claim 1, wherein the housing sheath portion comprises an expansion relief that allows outward circumferential expansion of the housing sheath portion during assembly over the housing.

13. The implantable medical device of claim 1, further comprising:
a distal electrode;
a proximal electrode;
a pacing circuit enclosed by the housing and electrically coupled to the distal electrode and the proximal electrode; and
a control circuit coupled to the pacing circuit and configured to control the pacing circuit to deliver cardiac pacing pulses via the distal electrode and the proximal electrode.

14. The implantable medical device of claim 1, further comprising:
a distal assembly comprising a distal electrode and at least one slot;
a proximal electrode along the outer sidewall of the housing;
a pacing circuit enclosed by the housing and electrically coupled to the distal electrode and the proximal electrode;
a control circuit coupled to the pacing circuit and configured to control the pacing circuit to deliver cardiac pacing pulses via the distal electrode and the proximal electrode;
wherein the fixation member portion comprises at least one tine having a tissue piercing distal tip, the at least one tine extending through the at least one slot with the tissue piercing distal tip retained within the at least one slot in the first position and advanced out of the at least one slot in the second position for penetrating body tissue at the implant site.

15. A fixation sheath for an implantable medical device, the fixation sheath comprising:
a housing sheath portion configured to extend along an outer sidewall of a housing of the implantable medical device, the implantable medical device enclosing electronic circuitry;
a fixation member portion extending from the housing sheath portion;
wherein the housing sheath portion is advanceable from a first position to a second position along the outer sidewall of the housing, the fixation member portion being retracted toward the proximal end of the housing in the first position and deployed to extend away from the distal end of the housing in the second position for anchoring the implantable medical device at an implant site; and
a delivery tool interface member comprising:
a flange extending proximally from the housing sheath portion; and
a head extending proximally from a proximal end of the flange and defining an axial recess disposed in a proximal surface of the head, wherein the head comprises a lateral rod extending across the axial recess,
wherein the flange or the head define a surface configured to interface with a pushing surface of a delivery tool for advancing the housing sheath portion from the first position to the second position, and
wherein the axial recess is configured to receive a tether of the delivery tool for retracting, by the lateral rod, the housing sheath portion from the second position to the first position.

16. The fixation sheath of claim 15, wherein the housing sheath portion circumscribes at least a portion of the outer sidewall of the housing.

17. The fixation sheath of claim 15, wherein the housing sheath portion comprises at least one window for exposing at least one sensor carried by the housing of the implantable medical device.

18. The fixation sheath of claim 15, wherein the housing sheath portion comprises a guide channel configured to receive and slide along a guide member protruding outward from the outer sidewall of the housing.

19. The fixation sheath of claim 18, wherein the guide channel is non-linear.

20. The fixation sheath of claim 18, wherein:
the fixation member portion comprises at least one helical tine having a winding pitch;
the guide channel is a helical guide channel having a pitch corresponding to the winding pitch of the helical tine; and
the housing sheath portion is advanceable from the first position to the second position by rotating the housing sheath portion relative to the housing such that the helical guide channel slides along the guide member.

21. The fixation sheath of claim 18, wherein the guide channel comprises a distal end defining a stop for interfacing with the guide member to prevent over-retraction of the fixation sheath relative to the housing.

22. The fixation sheath of claim 15, further comprising a proximal end that interfaces with a proximal end of the housing in the second position of the housing sheath portion.

23. The fixation sheath of claim 15, wherein the fixation member portion comprises at least one tine having a distal tip, the at least one tine configured to be retracted within a respective slot of a distal assembly coupled to the housing distal end in the first position and extended out of the at least one slot in the second position.

24. The fixation sheath of claim 15, wherein the fixation member portion comprises a plurality of tines that are elastically deformable from an extended position alongside the outer sidewall of the housing when the housing sheath portion is in the first position to a normally curved position when the housing sheath portion is advanced to the second position.

25. The fixation sheath of claim 15, wherein the housing sheath portion comprises an expansion relief that allows outward circumferential expansion of the housing sheath portion during assembly over the housing.

26. An implantable medical device system, comprising:
an implantable medical device comprising:
a housing having a proximal end, a distal end, and an outer sidewall extending from the proximal end to the distal end; and
a fixation sheath comprising:
a housing sheath portion extending along the outer sidewall of the housing,
a fixation member portion extending from the housing sheath portion, and
a delivery tool interface member coupled to the housing sheath portion, wherein the delivery tool interface member comprises:
a flange extending proximally from the housing sheath portion; and
a head extending proximally from a proximal end of the flange and defining an axial recess disposed in a proximal surface of the head, wherein the head comprises a lateral rod extending across the axial recess,
wherein the housing sheath portion is advanceable from a first position to a second position along the outer sidewall of the housing, the fixation member portion being retracted toward the proximal end of the housing in the first position and deployed to extend away from the distal end of the housing in the second position for anchoring the implantable medical device at an implant site; and
a delivery tool comprising:
a receptacle for retaining the housing with the fixation sheath in the first position;
an advancement tool configured to engage the flange or the head of the delivery tool interface member for advancing the housing sheath portion from the first position to the second position; and
a tether configured to engage the the lateral rod of the head of the delivery tool interface member for retracting the housing sheath portion from the second position to the first position.

27. The system of claim 26, wherein the tether comprises an elongated body having torsional resistance for transferring torque from a proximal tether end to the delivery tool interface member for advancing the housing sheath portion from the first position to the second position by rotating the housing sheath portion relative to the housing.

28. The system of claim 26, wherein the delivery tool comprises a distal face, and wherein the implantable medical device comprises a distal assembly coupled to the housing distal end, the distal assembly comprising a proximal face for interfacing with the delivery tool distal face for advancing the implantable medical device to an implant site.

29. The implantable medical device of claim 1, wherein the head further defines a circumferential recess disposed between a proximal end of the head and the proximal end of the flange.

30. The fixation sheath of claim 15, wherein head further defines a circumferential recess disposed between a proximal end of the head and the proximal end of the flange.

* * * * *